US007855060B2

(12) United States Patent
Filippov et al.

(10) Patent No.: US 7,855,060 B2
(45) Date of Patent: Dec. 21, 2010

(54) **METHOD FOR PRODUCING AN L-AMINO ACID USING A BACTERIUM OF THE *ENTEROBACTERIACEAE* FAMILY BY INACTIVATING A GENE ENCODING A TOXIN OF A BACTERIAL TOXIN-ANTITOXIN PAIR**

(75) Inventors: Dmitriy Vladimirovich Filippov, Moscow (RU); Elvira Borisovna Voroshilova, Moscow (RU); Mikhail Markovich Gusyatiner, Moscow (RU); Konstantin Vyacheslavovich Rybak, Moscow (RU); Marina Evgenievna Sheremeteva, Moscow (RU); Aleksandra Yurievna Skorokhodova, Moscow (RU); Vitaly Grigorievich Paraskevov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 377 days.

(21) Appl. No.: 11/830,974

(22) Filed: Jul. 31, 2007

(65) Prior Publication Data

US 2008/0113416 A1     May 15, 2008

Related U.S. Application Data

(63) Continuation of application No. PCT/JP2006/303215, filed on Feb. 16, 2006.

(60) Provisional application No. 60/723,929, filed on Oct. 6, 2005, provisional application No. 60/714,844, filed on Sep. 8, 2005, provisional application No. 60/714,849, filed on Sep. 8, 2005, provisional application No. 60/714,848, filed on Aug. 9, 2005.

(30) Foreign Application Priority Data

| Feb. 18, 2005 | (RU) | ............................. | 2005104460 |
| Feb. 18, 2005 | (RU) | ............................. | 2005104461 |
| Feb. 18, 2005 | (RU) | ............................. | 2005104462 |
| Mar. 10, 2005 | (RU) | ............................. | 2005106344 |
| Mar. 31, 2005 | (RU) | ............................. | 2005109258 |
| Aug. 9, 2005 | (RU) | ............................. | 2005125291 |

(51) Int. Cl.
*C12P 13/04* (2006.01)
*C12P 21/00* (2006.01)
*C12N 1/21* (2006.01)
*C12N 15/00* (2006.01)
*C07K 14/00* (2006.01)
*C07H 21/00* (2006.01)

(52) U.S. Cl. ................. 435/106; 435/252.33; 435/69.1; 435/440; 530/350; 536/23.1

(58) Field of Classification Search ............... 435/320.1, 435/69.1, 325, 252.33, 106, 440, 252.3; 530/350; 536/23.1
See application file for complete search history.

(56) References Cited

U.S. PATENT DOCUMENTS

| 6,960,455 | B2 | 11/2005 | Livshits et al. |
| 7,138,266 | B2 | 11/2006 | Debabov et al. |
| 7,179,623 | B2 | 2/2007 | Livshits et al. |
| 7,186,531 | B2 | 3/2007 | Akhverdian et al. |
| 2003/0148473 | A1 | 8/2003 | Livshits et al. |
| 2004/0132165 | A1 | 7/2004 | Akhverdian et al. |
| 2005/0048631 | A1 | 3/2005 | Klyachko et al. |
| 2005/0054061 | A1 | 3/2005 | Klyachko et al. |
| 2005/0112731 | A1 | 5/2005 | Kashiwagi et al. |
| 2005/0176033 | A1 | 8/2005 | Klyachko et al. |
| 2005/0191684 | A1 | 9/2005 | Zimenkov et al. |
| 2005/0214911 | A1 | 9/2005 | Marchenko et al. |
| 2005/0239175 | A1 | 10/2005 | Tabolina et al. |
| 2006/0014257 | A1 | 1/2006 | Katashkina et al. |
| 2006/0035346 | A1 | 2/2006 | Savrasova et al. |
| 2006/0035348 | A1 | 2/2006 | Gulevich et al. |
| 2006/0040365 | A1 | 2/2006 | Kozlov et al. |
| 2006/0063240 | A1 | 3/2006 | Katashkina et al. |
| 2006/0088919 | A1 | 4/2006 | Rybak et al. |
| 2006/0141586 | A1 | 6/2006 | Rybak et al. |
| 2006/0160192 | A1 | 7/2006 | Rybak et al. |
| 2007/0184532 | A1 | 8/2007 | Klyachko et al. |

OTHER PUBLICATIONS

Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247, 1991.*
Zhou et al., Cell Mol Life Sci 63(19-20):2260-2290, 2006.*
Kozak, M., Gene 234:187-208, 1999.*
Aizenman, E., et al., "An *Escherichia coli* chromosomal "addiction module" regulated by 3',5'-bispyrophosphate: A model for programmed bacterial cell death," Proc. Natl. Acad. Sci. USA 1996;93:6059-6063.
Brown, J. M., et al., "A Novel Family of *Escherichia coli* Toxin-Antitoxin Gene Pairs," J. Bacteriol. 2003;185(22):6600-6608.
Chang, D-E., et al., "Gene expression profiling of *Escherichia coli* growth transitions: an expanded stringent response model," Mol. Microbiol. 2002;45(2):289-306.
Cherny, I., et al., "The YefM Antitoxin Defines a Family of Natively Unfolded Proteins, Implication as a Novel Antibacterial Target," J. Biol. Chem. 2004;279(9):8252-8261.
Christensen, S. K., et al., "Overproduction of the Lon protease triggers inhibition of translation in *Escherichia coli*: involvement of the yefM-yoeB toxin-antitoxin system," Mol. Microbiol. 2004;51(6):1705-1717.
Christensen, S. K., et al., "RelE, a global inhibitor of translation, is activated during nutritional stress," PNAS 2001;98(25):14328-14333.

(Continued)

*Primary Examiner*—Delia M Ramirez
(74) *Attorney, Agent, or Firm*—Shelly Guest Cermak; Cermak Nakajima LLP

(57) ABSTRACT

The present invention provides a method for producing an L-amino acid using a bacterium of the Enterobacteriaceae family, particularly a bacterium belonging the genus *Escherichia* or *Pantoea*, wherein said bacterium has attenuated expression of a gene encoding a toxin of a bacterial toxin-antitoxin pair.

5 Claims, 13 Drawing Sheets

OTHER PUBLICATIONS

Christensen, S. K., et al., "Toxin-antitoxin Loci as Stress-response-elements: ChpAK/MazF and ChpBK Cleave Translated RNAs and are Counteracted by tmRNA," J. Mol. Biol. 2003;332:809-819.

Christensen, S. K., et al., "RelE toxins from Bacteria and Archaea cleave mRNAs on translating ribosomes, which are rescued by tmRNA," Mol. Microbiol. 2003;48(5):1389-1400.

Falla, T. J., et al., "Joint Tolerance to β-Lactam and Fluoroquinolone Antibiotics in *Escherichia coli* Results from Overexpression of *hipA*," Antimicrob. Agents Chemother. 1998;42(12):3282-3284.

Galvani, C., et al., "Purification of the RelB and RelE Proteins of *Escherichia coli*: RelE Binds to RelB and to Ribosomes," J. Bacteriol. 2001;183(8):2700-2703.

Gerdes, K., "Toxin-Antitoxin Modules May Regulate Synthesis of Macromolecules during Nutritional Stress," J. Bacteriol. 2000;182(3):561-572.

Gotfredsen, M., et al., "The *Escherichia coli relBE* genes belong to a new toxin-antitoxin gene family," Mol. Microbiol. 1998;29(4):1065-1076.

Grady, R., et al., "Axe-Txe, a broad-spectrum proteic toxin-antitoxin system specified by a multidrug-resistant, clinical isolate of *Enterococcus faecium*," Mol. Microbiol. 2003;47(5):1419-1432.

Keren, I., et al., "Specialized Persister Cells and the Mechanism of Multidrug Tolerance in *Escherichia coli*," J. Bacteriol. 2004; 186(24):8172-8180.

Korch, S. B., et al., "Characterization of the *hipA7* allele of *Escherichia coli* and evidence that high persistence is governed by (p)ppGpp synthesis," Mol. Microbiol. 2003;50(4):1199-1213.

Muñoz-Gómez, A. J., et al., "Insights into the specificity of RNA cleavage by the *Escherichia coli* MazF toxin," FEBS Letters 2004;567:316-320.

Pedersen, K., et al., "Rapid induction and reversal of a bacteriostatic condition by controlled expression of toxins and antitoxins," Mol. Microbiol. 2002;45(2)501-510.

Pedersen, K., et al., "The Bacterial Toxin RelE Displays Codon-Specific Cleavage of mRNAs in the Ribosomal A Site," Cell 2003;112:131-140.

Rida, S., et al., "Amplification of a Novel Gene, *sanA*, Abolishes a Vancomycin-Sensitive Defect in *Escherichia coli*," J. Bacteriol. 1996;178(1):94-102.

Sat, B., et al., "Programmed Cell Death in *Escherichia coli*: Some Antibiotics Can Trigger *mazEF* Lethality," J. Bacteriol. 2001;183(6):2041-2045.

Sat, B., et al., "The *Escherichia coli mazEF* Suicide Module Mediates Thymineless Death," J. Bacteriol. 2003;185(6):1803-1807.

Scherrer, R., et al., "Conditional Impairment of Cell Division and Altered Lethality in *hipA* Mutants of *Escherichia coli* K-12," J. Bacteriol. 1988;170(8):3321-3326.

Zhang, J., et al., "Characterization of the Interactions within the *mazEF* Addiction Module of *Escherichia coli*," J. Biol. Chem. 2003;278(34):32300-32306.

Zhang, Y., et al., "MazF Cleaves Cellular mRNAs Specifically at ACA to Block Protein Synthesis in *Escherichia coli*," Mol. Cell. 2003;12:912-923.

U.S. Appl. No. 60/586,222, filed Jul. 9, 2004, Akhverdian et al.
U.S. Appl. No. 60/587,492, filed Jul. 14, 2004, Klyachko et al.
U.S. Appl. No. 60/604,698, filed Aug. 27, 2004, Zimenkov et al.
U.S. Appl. No. 60/610,545, filed Sep. 17, 2004, Marchenko et al.
U.S. Appl. No. 60/644,562, filed Jan. 19, 2005, Rybak et al.
U.S. Appl. No. 60/673,807, filed Apr. 22, 2005, Rybak et al.
U.S. Appl. No. 60/693,507, filed Jun. 24, 2005, Rybak et al.
U.S. Appl. No. 60/693,509, filed Jun. 24, 2005, Sheremet'eva et al.
U.S. Appl. No. 60/703,414, filed Jul. 29, 2005, Ptitsyn et al.
U.S. Appl. No. 60/703,444, filed Jul. 29, 2005, Rybak et al.
U.S. Appl. No. 60/703,426, filed Jul. 29, 2005, Rybak et al.
U.S. Appl. No. 60/714,843, filed Sep. 8, 2005, Filippov et al.
U.S. Appl. No. 60/714,844, filed Sep. 8, 2005, Filippov et al.
U.S. Appl. No. 60/714,848, filed Sep. 8, 2005, Filippov et al.
U.S. Appl. No. 60/714,849, filed Sep. 8, 2005, Filippov et al.
U.S. Appl. No. 60/723,566, filed Oct. 5, 2005, Rybak et al.
U.S. Appl. No. 60/723,923, filed Oct. 6, 2005, Filippov et al.
U.S. Appl. No. 60/723,924, filed Oct. 6, 2005, Rybak et al.
U.S. Appl. No. 60/723,925, filed Oct. 6, 2005, Rybak et al.
U.S. Appl. No. 60/723,928, filed Oct. 6, 2005, Rybak et al.
U.S. Appl. No. 60/723,929, filed Oct. 6, 2005, Filippov et al.
U.S. Appl. No. 60/736,830, filed Nov. 16, 2005, Filippov et al.
U.S. Appl. No. 11/275,507, filed Jan. 11, 2006, Ptitsyn et al.
U.S. Appl. No. 60/743,222, filed Feb. 3, 2006, Rybak et al.
U.S. Appl. No. 60/743,223, filed Feb. 3, 2006, Rybak et al.
U.S. Appl. No. 60/743,229, filed Feb. 3, 2006, Rybak et al.
U.S. Appl. No. 60/743,257, filed Feb. 9, 2006, Rybak et al.
U.S. Appl. No. 60/743,258, filed Feb. 9, 2006, Rybak et al.
U.S. Appl. No. 60/806,819, filed Jul. 10, 2006, Rybak et al.
U.S. Appl. No. 60/807,842, filed Jul. 20, 2006, Filippov et al.
U.S. Appl. No. 60/807,843, filed Jul. 20, 2006, Filippov et al.
U.S. Appl. No. 60/807,845, filed Jul. 20, 2006, Filippov et al.
U.S. Appl. No. 60/826,820, filed Sep. 25, 2006, Kotliarova et al.
U.S. Appl. No. 11/536,863, filed Sep. 29, 2006, Zakataeva et al.
U.S. Appl. No. 60/829,697, filed Oct. 17, 2006, Rybak et al.
U.S. Appl. No. 60/829,706, filed Oct. 17, 2006, Filippov et al.
U.S. Appl. No. 60/829,923, filed Oct. 18, 2006, Filippov et al.
U.S. Appl. No. 60/829,926, filed Oct. 18, 2006, Rybak et al.
U.S. Appl. No. 60/867,151, filed Nov. 24, 2006, Rybak et al.
U.S. Appl. No. 60/885,671, filed Jan. 19, 2007, Ptitsyn et al.
U.S. Appl. No. 60/894,996, filed Mar. 15, 2007, Rybak et al.
U.S. Appl. No. 11/761,465, filed Jun. 12, 2007, Livshits et al.
U.S. Appl. No. 11/830,961, filed Jul. 31, 2007, Filippov et al.
U.S. Appl. No. 60/954,663, filed Aug. 8, 2007, Filippov et al.
U.S. Appl. No. 60/954,668, filed Aug. 8, 2007, Samsonov et al.
U.S. Appl. No. 60/955,968, filed Aug. 15, 2007, Filippov et al.

Li, G-Y, et al., "Characterization of Dual Substrate Binding Sites in the Homodimeric Structure of *Escherichia coli* mRNA Interferase MazF," J. Mol. Biol. 2006;357:139-150.

International Search Report for PCT Patent App. No. PCT/JP2006/303215 (Jul. 17, 2006).

\* cited by examiner

Obtained PCR product (1152 bp)

Obtained PCR product (1152 bp)

Obtained PCR product (1152 bp)

Obtained PCR product (1699 bp)

SEQUENCE LISTING

```
<160> NUMBER OF SEQ ID NOS: 58

<210> SEQ ID NO 1
<211> LENGTH: 279
<212> TYPE: DNA
<213> ORGANISM: Escherichia coli
<220> FEATURE:
<221> NAME/KEY: CDS
<222> LOCATION: (1)..(279)

<400> SEQUENCE: 1 atg aac tgt aca aaa gag gag att gac atg cgt aca att agc tac agc      48
Met Asn Cys Thr Lys Glu Glu Ile Asp Met Arg Thr Ile Ser Tyr Ser
1               5                   10                  15 gaa gcg cgt cag aat ttg tcg gca aca atg atg aaa gcc gtt gaa gat      96
Glu Ala Arg Gln Asn Leu Ser Ala Thr Met Met Lys Ala Val Glu Asp
                20                  25                  30 cat gcc ccg atc ctt att act cgt cag aat gga gag gct tgt gtt ctg      144
His Ala Pro Ile Leu Ile Thr Arg Gln Asn Gly Glu Ala Cys Val Leu
            35                  40                  45 atg tca ctc gaa gaa tac aac tcg ctg gaa gag acg gct tat cta ctg      192
Met Ser Leu Glu Glu Tyr Asn Ser Leu Glu Glu Thr Ala Tyr Leu Leu
        50                  55                  60 cgc tcc ccc gct aac gcc cgg aga ttg atg gac tca atc gat agc ctg      240
Arg Ser Pro Ala Asn Ala Arg Arg Leu Met Asp Ser Ile Asp Ser Leu
65                  70                  75                  80 aaa tca ggc aaa gga acg gaa aag gac atc att gag tga                  279
Lys Ser Gly Lys Gly Thr Glu Lys Asp Ile Ile Glu
                85                  90

<210> SEQ ID NO 2
<211> LENGTH: 92
<212> TYPE: PRT
<213> ORGANISM: Escherichia coli

<400> SEQUENCE: 2

Met Asn Cys Thr Lys Glu Glu Ile Asp Met Arg Thr Ile Ser Tyr Ser
1               5                   10                  15

Glu Ala Arg Gln Asn Leu Ser Ala Thr Met Met Lys Ala Val Glu Asp
                20                  25                  30

His Ala Pro Ile Leu Ile Thr Arg Gln Asn Gly Glu Ala Cys Val Leu
            35                  40                  45

Met Ser Leu Glu Glu Tyr Asn Ser Leu Glu Glu Thr Ala Tyr Leu Leu
        50                  55                  60
```

```
Arg Ser Pro Ala Asn Ala Arg Arg Leu Met Asp Ser Ile Asp Ser Leu
 65                  70                  75                  80

Lys Ser Gly Lys Gly Thr Glu Lys Asp Ile Ile Glu
                 85                  90

<210> SEQ ID NO 3
<211> LENGTH: 57
<212> TYPE: DNA
<213> ORGANISM: Artificial
<220> FEATURE:
<223> OTHER INFORMATION: primer

<400> SEQUENCE: 3
attaataaat agttaattaa cgctcatcat tgtacatagt aagccagtat acactcc      57

<210> SEQ ID NO 4
<211> LENGTH: 57
<212> TYPE: DNA
<213> ORGANISM: Artificial
<220> FEATURE:
<223> OTHER INFORMATION: primer

<400> SEQUENCE: 4
taaccaccct aacccgacaa ttgcgacctt tttcatttaa gggcaccaat aactgcc      57

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
tttcgtctca ctgacaatac c                                             21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
gaagcagata gctatcaatg c                                             21

<210> SEQ ID NO 7
<211> LENGTH: 279
<212> TYPE: DNA
<213> ORGANISM: Escherichia coli
<220> FEATURE:
<221> NAME/KEY: CDS
<222> LOCATION: (1)..(279)

<400> SEQUENCE: 7 atg att caa agg gat att gaa tac tcg gga caa tat tca aag gat gta    48
Met Ile Gln Arg Asp Ile Glu Tyr Ser Gly Gln Tyr Ser Lys Asp Val
 1               5                  10                  15 aaa ctt gca caa aag cgt cat aag gat atg aat aaa ttg aaa tat ctt    96
Lys Leu Ala Gln Lys Arg His Lys Asp Met Asn Lys Leu Lys Tyr Leu
             20                  25                  30 atg acg ctt ctt atc aat aat act tta ccg ctt cca gct gtt tat aaa   144
Met Thr Leu Leu Ile Asn Asn Thr Leu Pro Leu Pro Ala Val Tyr Lys
         35                  40                  45 gac cac ccg ctg caa ggt tca tgg aaa ggt tat cgc gat gct cat gtc   192
```

```
Asp His Pro Leu Gln Gly Ser Trp Lys Gly Tyr Arg Asp Ala His Val
     50                  55                  60 gaa ccg gac tgg atc ctg att tac aaa ctt acc gat aaa ctt tta cga    240
Glu Pro Asp Trp Ile Leu Ile Tyr Lys Leu Thr Asp Lys Leu Leu Arg
 65                  70                  75                  80 ttt gag aga act gga act cac gcg gcg ctc ttt ggg taa                279
Phe Glu Arg Thr Gly Thr His Ala Ala Leu Phe Gly
                 85                  90

<210> SEQ ID NO 8
<211> LENGTH: 92
<212> TYPE: PRT
<213> ORGANISM: Escherichia coli

<400> SEQUENCE: 8

Met Ile Gln Arg Asp Ile Glu Tyr Ser Gly Gln Tyr Ser Lys Asp Val
 1               5                  10                  15

Lys Leu Ala Gln Lys Arg His Lys Asp Met Asn Lys Leu Lys Tyr Leu
                 20                  25                  30

Met Thr Leu Leu Ile Asn Asn Thr Leu Pro Leu Pro Ala Val Tyr Lys
             35                  40                  45

Asp His Pro Leu Gln Gly Ser Trp Lys Gly Tyr Arg Asp Ala His Val
     50                  55                  60

Glu Pro Asp Trp Ile Leu Ile Tyr Lys Leu Thr Asp Lys Leu Leu Arg
 65                  70                  75                  80

Phe Glu Arg Thr Gly Thr His Ala Ala Leu Phe Gly
                 85                  90

<210> SEQ ID NO 9
<211> LENGTH: 57
<212> TYPE: DNA
<213> ORGANISM: Artificial
<220> FEATURE:
<223> OTHER INFORMATION: primer

<400> SEQUENCE: 9
atggctgcta acgcgtttgt tcgcgcccga atcgattagt aagccagtat acactcc     57

<210> SEQ ID NO 10
<211> LENGTH: 57
<212> TYPE: DNA
<213> ORGANISM: Artificial
<220> FEATURE:
<223> OTHER INFORMATION: primer

<400> SEQUENCE: 10
ttacccaaag agcgccgcgt gagttccagt tctctcttaa gggcaccaat aactgcc     57

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
tatacagcac aggagatacc c                                            21

<210> SEQ ID NO 12
<211> LENGTH: 21
<212> TYPE: DNA
<213> ORGANISM: Artificial
<220> FEATURE:
```

-continued

```
<223> OTHER INFORMATION: primer

<400> SEQUENCE: 12
tggaaggctc acattatcac c                                              21

<210> SEQ ID NO 13
<211> LENGTH: 336
<212> TYPE: DNA
<213> ORGANISM: Escherichia coli
<220> FEATURE:
<221> NAME/KEY: CDS
<222> LOCATION: (1)..(336)

<400> SEQUENCE: 13 atg gta agc cga tac gta ccc gat atg ggc gat ctg att tgg gtt gat       48
Met Val Ser Arg Tyr Val Pro Asp Met Gly Asp Leu Ile Trp Val Asp
1               5                   10                  15 ttt gac ccg aca aaa ggt agc gag caa gct gga cat cgt cca gct gtt       96
Phe Asp Pro Thr Lys Gly Ser Glu Gln Ala Gly His Arg Pro Ala Val
            20                  25                  30 gtc ctg agt cct ttc atg tac aac aac aaa aca ggt atg tgt ctg tgt      144
Val Leu Ser Pro Phe Met Tyr Asn Asn Lys Thr Gly Met Cys Leu Cys
        35                  40                  45 gtt cct tgt aca acg caa tca aaa gga tat ccg ttc gaa gtt gtt tta      192
Val Pro Cys Thr Thr Gln Ser Lys Gly Tyr Pro Phe Glu Val Val Leu
    50                  55                  60 tcc ggt cag gaa cgt gat ggc gta gcg tta gct gat cag gta aaa agt      240
Ser Gly Gln Glu Arg Asp Gly Val Ala Leu Ala Asp Gln Val Lys Ser
65                  70                  75                  80 atc gcc tgg cgg gca aga gga gca acg aag aaa gga aca gtt gcc cca      288
Ile Ala Trp Arg Ala Arg Gly Ala Thr Lys Lys Gly Thr Val Ala Pro
                85                  90                  95 gag gaa tta caa ctc att aaa gcc aaa att aac gta ctg att ggg tag      336
Glu Glu Leu Gln Leu Ile Lys Ala Lys Ile Asn Val Leu Ile Gly
            100                 105                 110

<210> SEQ ID NO 14
<211> LENGTH: 111
<212> TYPE: PRT
<213> ORGANISM: Escherichia coli

<400> SEQUENCE: 14

Met Val Ser Arg Tyr Val Pro Asp Met Gly Asp Leu Ile Trp Val Asp
1               5                   10                  15

Phe Asp Pro Thr Lys Gly Ser Glu Gln Ala Gly His Arg Pro Ala Val
            20                  25                  30

Val Leu Ser Pro Phe Met Tyr Asn Asn Lys Thr Gly Met Cys Leu Cys
        35                  40                  45

Val Pro Cys Thr Thr Gln Ser Lys Gly Tyr Pro Phe Glu Val Val Leu
    50                  55                  60

Ser Gly Gln Glu Arg Asp Gly Val Ala Leu Ala Asp Gln Val Lys Ser
65                  70                  75                  80

Ile Ala Trp Arg Ala Arg Gly Ala Thr Lys Lys Gly Thr Val Ala Pro
                85                  90                  95

Glu Glu Leu Gln Leu Ile Lys Ala Lys Ile Asn Val Leu Ile Gly
            100                 105                 110

<210> SEQ ID NO 15
<211> LENGTH: 57
<212> TYPE: DNA
<213> ORGANISM: Artificial
```

```
<220> FEATURE:
<223> OTHER INFORMATION: primer

<400> SEQUENCE: 15
atgatccaca gtagcgtaaa gcgttgggga aattcatagt aagccagtat acactcc        57

<210> SEQ ID NO 16
<211> LENGTH: 57
<212> TYPE: DNA
<213> ORGANISM: Artificial
<220> FEATURE:
<223> OTHER INFORMATION: primer

<400> SEQUENCE: 16
ctacccaatc agtacgttaa ttttggcttt aatgagttaa gggcaccaat aactgcc        57

<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
tgtatctaca tatgatagcg g                                               21

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
aattgtcctg aaaattgcgg g                                               21

<210> SEQ ID NO 19
<211> LENGTH: 288
<212> TYPE: DNA
<213> ORGANISM: Escherichia coli
<220> FEATURE:
<221> NAME/KEY: CDS
<222> LOCATION: (1)..(288)

<400> SEQUENCE: 19 atg gcg tat ttt ctg gat ttt gac gag cgg gca cta aag gaa tgg cga      48
Met Ala Tyr Phe Leu Asp Phe Asp Glu Arg Ala Leu Lys Glu Trp Arg
1               5                   10                  15 aag ctg ggc tcg acg gta cgt gaa cag ttg aaa aag aag ctg gtt gaa      96
Lys Leu Gly Ser Thr Val Arg Glu Gln Leu Lys Lys Lys Leu Val Glu
            20                  25                  30 gta ctt gag tca ccc cgg att gaa gca aac aag ctc cgt ggt atg cct     144
Val Leu Glu Ser Pro Arg Ile Glu Ala Asn Lys Leu Arg Gly Met Pro
        35                  40                  45 gat tgt tac aag att aag ctc cgg tct tca ggc tat cgc ctt gta tac     192
Asp Cys Tyr Lys Ile Lys Leu Arg Ser Ser Gly Tyr Arg Leu Val Tyr
    50                  55                  60 cag gtt ata gac gag aaa gtt gtc gtt ttc gtg att tct gtt ggg aaa     240
Gln Val Ile Asp Glu Lys Val Val Val Phe Val Ile Ser Val Gly Lys
65                  70                  75                  80 aga gaa cgc tcg gaa gta tat agc gag gcg gtc aaa cgc att ctc tga     288
Arg Glu Arg Ser Glu Val Tyr Ser Glu Ala Val Lys Arg Ile Leu
                85                  90                  95
```

```
<210> SEQ ID NO 20
<211> LENGTH: 95
<212> TYPE: PRT
<213> ORGANISM: Escherichia coli

<400> SEQUENCE: 20

Met Ala Tyr Phe Leu Asp Phe Asp Glu Arg Ala Leu Lys Glu Trp Arg
1               5                   10                  15

Lys Leu Gly Ser Thr Val Arg Glu Gln Leu Lys Lys Leu Val Glu
            20                  25                  30

Val Leu Glu Ser Pro Arg Ile Glu Ala Asn Lys Leu Arg Gly Met Pro
        35                  40                  45

Asp Cys Tyr Lys Ile Lys Leu Arg Ser Ser Gly Tyr Arg Leu Val Tyr
    50                  55                  60

Gln Val Ile Asp Glu Lys Val Val Val Phe Val Ile Ser Val Gly Lys
65                  70                  75                  80

Arg Glu Arg Ser Glu Val Tyr Ser Glu Ala Val Lys Arg Ile Leu
                85                  90                  95

<210> SEQ ID NO 21
<211> LENGTH: 57
<212> TYPE: DNA
<213> ORGANISM: Artificial
<220> FEATURE:
<223> OTHER INFORMATION: primer

<400> SEQUENCE: 21
atgggtagca ttaacctgcg tattgacgat gaactttagt aagccagtat acactcc      57

<210> SEQ ID NO 22
<211> LENGTH: 57
<212> TYPE: DNA
<213> ORGANISM: Artificial
<220> FEATURE:
<223> OTHER INFORMATION: primer

<400> SEQUENCE: 22
tcagagaatg cgtttgaccg cctcgctata tacttcttaa gggcaccaat aactgcc      57

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
tgacatttgt aattacaaga gg                                            22

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
aacagagatg tcatgctttg g                                             21

<210> SEQ ID NO 25
<211> LENGTH: 375
<212> TYPE: DNA
<213> ORGANISM: Escherichia coli
<220> FEATURE:
```

<221> NAME/KEY: CDS
<222> LOCATION: (1)..(375)

<400> SEQUENCE: 25

```
atg aaa aca tta cct gta tta ccc ggg cag gcg gcc agt tct cgc ccg      48
Met Lys Thr Leu Pro Val Leu Pro Gly Gln Ala Ala Ser Ser Arg Pro
1               5                   10                  15 tct cct gtt gaa atc tgg cag ata ctg ctg tcc cga ctg ctg gac cag      96
Ser Pro Val Glu Ile Trp Gln Ile Leu Leu Ser Arg Leu Leu Asp Gln
            20                  25                  30 cac tat ggc ctc aca ctg aat gac aca cct ttt gcc gat gaa cgt gtg     144
His Tyr Gly Leu Thr Leu Asn Asp Thr Pro Phe Ala Asp Glu Arg Val
        35                  40                  45 att gag cag cat att gag gca ggc att tca ctg tgt gat gcg gtg aac     192
Ile Glu Gln His Ile Glu Ala Gly Ile Ser Leu Cys Asp Ala Val Asn
50                  55                  60 ttt ctc gtg gaa aaa tac gcg ctg gtg cgt acc gac cag ccg gga ttc     240
Phe Leu Val Glu Lys Tyr Ala Leu Val Arg Thr Asp Gln Pro Gly Phe
65                  70                  75                  80 agc gcc tgt acc cgc tct cag tta ata aac agc atc gat atc ctc cgg     288
Ser Ala Cys Thr Arg Ser Gln Leu Ile Asn Ser Ile Asp Ile Leu Arg
                85                  90                  95 gct cgc agg gcg acc ggc ctg atg acc cgc gac aat tac aga acg gta     336
Ala Arg Arg Ala Thr Gly Leu Met Thr Arg Asp Asn Tyr Arg Thr Val
            100                 105                 110 aat aac att acc ctg ggt aag tat ccg gag gcg aaa tga                 375
Asn Asn Ile Thr Leu Gly Lys Tyr Pro Glu Ala Lys
        115                 120
```

<210> SEQ ID NO 26
<211> LENGTH: 124
<212> TYPE: PRT
<213> ORGANISM: Escherichia coli

<400> SEQUENCE: 26

```
Met Lys Thr Leu Pro Val Leu Pro Gly Gln Ala Ala Ser Ser Arg Pro
1               5                   10                  15

Ser Pro Val Glu Ile Trp Gln Ile Leu Leu Ser Arg Leu Leu Asp Gln
            20                  25                  30

His Tyr Gly Leu Thr Leu Asn Asp Thr Pro Phe Ala Asp Glu Arg Val
        35                  40                  45

Ile Glu Gln His Ile Glu Ala Gly Ile Ser Leu Cys Asp Ala Val Asn
50                  55                  60

Phe Leu Val Glu Lys Tyr Ala Leu Val Arg Thr Asp Gln Pro Gly Phe
65                  70                  75                  80

Ser Ala Cys Thr Arg Ser Gln Leu Ile Asn Ser Ile Asp Ile Leu Arg
                85                  90                  95

Ala Arg Arg Ala Thr Gly Leu Met Thr Arg Asp Asn Tyr Arg Thr Val
            100                 105                 110

Asn Asn Ile Thr Leu Gly Lys Tyr Pro Glu Ala Lys
        115                 120
```

<210> SEQ ID NO 27
<211> LENGTH: 57
<212> TYPE: DNA
<213> ORGANISM: Artificial
<220> FEATURE:
<223> OTHER INFORMATION: primer

<400> SEQUENCE: 27

```
gaccattctt agccgatttt ctgtaaggat tttatctagt aagccagtat acactcc        57
```

<210> SEQ ID NO 28
<211> LENGTH: 57
<212> TYPE: DNA
<213> ORGANISM: Artificial
<220> FEATURE:
<223> OTHER INFORMATION: primer

<400> SEQUENCE: 28

```
gcgcctgtac gttaacgctg tcggcttcca gtgtcattaa gggcaccaat aactgcc        57
```

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29

```
tgagtgggaa ttctgatgag c                                               21
```

<210> SEQ ID NO 30
<211> LENGTH: 21
<212> TYPE: DNA
<213> ORGANISM: Artificial
<220> FEATURE:
<223> OTHER INFORMATION: primer

<400> SEQUENCE: 30

```
tcaatgtcaa cgacaatgtg c                                               21
```

<210> SEQ ID NO 31
<211> LENGTH: 1323
<212> TYPE: DNA
<213> ORGANISM: Escherichia coli
<220> FEATURE:
<221> NAME/KEY: CDS
<222> LOCATION: (1)..(1323)

<400> SEQUENCE: 31

```
atg cct aaa ctt gtc act tgg atg aac aac cag cgg gta ggc gag tta       48
Met Pro Lys Leu Val Thr Trp Met Asn Asn Gln Arg Val Gly Glu Leu
1               5                   10                  15 acg aag tta gcc aac ggc gcg cac acc ttt aag tat gca ccg gag tgg       96
Thr Lys Leu Ala Asn Gly Ala His Thr Phe Lys Tyr Ala Pro Glu Trp
            20                  25                  30 tta gca agc cgt tat gcc aga ccg ttg tca ctt tcg ctg cca ttg cag      144
Leu Ala Ser Arg Tyr Ala Arg Pro Leu Ser Leu Ser Leu Pro Leu Gln
        35                  40                  45 agg ggg aat atc acc tct gat gcc gta ttt aac ttc ttc gat aac ctg      192
Arg Gly Asn Ile Thr Ser Asp Ala Val Phe Asn Phe Phe Asp Asn Leu
    50                  55                  60 tta ccc gat agc ccg att gta cgt gac cgg atc gtt aaa cgt tat cat      240
Leu Pro Asp Ser Pro Ile Val Arg Asp Arg Ile Val Lys Arg Tyr His
65                  70                  75                  80 gcc aaa tcc aga caa ccg ttt gat tta ttg tca gaa ata ggg cga gac      288
Ala Lys Ser Arg Gln Pro Phe Asp Leu Leu Ser Glu Ile Gly Arg Asp
                85                  90                  95 agc gtt ggt gcc gtg acg tta ata ccc gaa gac gaa acc gta acg cat      336
Ser Val Gly Ala Val Thr Leu Ile Pro Glu Asp Glu Thr Val Thr His
            100                 105                 110 ccg ata atg gca tgg gaa aag ctt act gaa gcc aga ctt gaa gaa gta      384
Pro Ile Met Ala Trp Glu Lys Leu Thr Glu Ala Arg Leu Glu Glu Val
```

-continued

```
            115                 120                 125
tta acg gct tat aaa gca gat atc ccg cta ggc atg att aga gaa gaa    432
Leu Thr Ala Tyr Lys Ala Asp Ile Pro Leu Gly Met Ile Arg Glu Glu
    130                 135                 140 aat gac ttt cgc atc tcg gtt gct ggc gca cag gag aag aca gca ctg    480
Asn Asp Phe Arg Ile Ser Val Ala Gly Ala Gln Glu Lys Thr Ala Leu
145                 150                 155                 160 ctc aga ata ggc aat gac tgg tgc att ccg aaa gga ata acg ccg acg    528
Leu Arg Ile Gly Asn Asp Trp Cys Ile Pro Lys Gly Ile Thr Pro Thr
                165                 170                 175 acg cac atc att aaa tta ccg att ggc gaa atc agg cag ccc aat gcg    576
Thr His Ile Ile Lys Leu Pro Ile Gly Glu Ile Arg Gln Pro Asn Ala
            180                 185                 190 acg ctc gat ctc agc caa agc gtt gat aat gag tat tac tgt ctg ctg    624
Thr Leu Asp Leu Ser Gln Ser Val Asp Asn Glu Tyr Tyr Cys Leu Leu
        195                 200                 205 ctg gcg aaa gaa ctt ggg ttg aat gtt ccg gac gca gaa atc att aaa    672
Leu Ala Lys Glu Leu Gly Leu Asn Val Pro Asp Ala Glu Ile Ile Lys
    210                 215                 220 gcg gga aat gtg cgc gcg tta gcg gtc gaa cgt ttt gac agg cgt tgg    720
Ala Gly Asn Val Arg Ala Leu Ala Val Glu Arg Phe Asp Arg Arg Trp
225                 230                 235                 240 aat gct gag cga acg gtt tta ctt cgc ttg cca cag gag gat atg tgt    768
Asn Ala Glu Arg Thr Val Leu Leu Arg Leu Pro Gln Glu Asp Met Cys
                245                 250                 255 cag aca ttc ggt tta cct tca tcg gtg aaa tat gaa tca gat gga ggc    816
Gln Thr Phe Gly Leu Pro Ser Ser Val Lys Tyr Glu Ser Asp Gly Gly
            260                 265                 270 cca ggc atc gcg cgg atc atg gct ttt ttg atg ggg tcc agc gag gcg    864
Pro Gly Ile Ala Arg Ile Met Ala Phe Leu Met Gly Ser Ser Glu Ala
        275                 280                 285 ctg aaa gat cgc tat gat ttt atg aaa ttc cag gtc ttc cag tgg ttg    912
Leu Lys Asp Arg Tyr Asp Phe Met Lys Phe Gln Val Phe Gln Trp Leu
    290                 295                 300 att ggc gca acg gac ggt cat gca aaa aac ttc tcc gta ttt att cag    960
Ile Gly Ala Thr Asp Gly His Ala Lys Asn Phe Ser Val Phe Ile Gln
305                 310                 315                 320 gct ggc ggc agt tat cga ctc acg cca ttt tac gac atc att tca gca   1008
Ala Gly Gly Ser Tyr Arg Leu Thr Pro Phe Tyr Asp Ile Ile Ser Ala
                325                 330                 335 ttt ccg gtc ctt ggc ggt acg gga ata cac atc agc gat ctc aaa ctg   1056
Phe Pro Val Leu Gly Gly Thr Gly Ile His Ile Ser Asp Leu Lys Leu
            340                 345                 350 gca atg ggg ctt aac gca tcc aaa ggc aaa aaa acg gca atc gat aaa   1104
Ala Met Gly Leu Asn Ala Ser Lys Gly Lys Lys Thr Ala Ile Asp Lys
        355                 360                 365 att tat ccg cga cat ttt ttg gcg aca gca aag gtg ctg aga ttc ccg   1152
Ile Tyr Pro Arg His Phe Leu Ala Thr Ala Lys Val Leu Arg Phe Pro
    370                 375                 380 gaa gtg cag atg cat gaa atc ctg agt gac ttt gcc aga atg att cca   1200
Glu Val Gln Met His Glu Ile Leu Ser Asp Phe Ala Arg Met Ile Pro
385                 390                 395                 400 gca gca ctg gat aac gtg aag act tca tta ccg aca gat ttt ccg gag   1248
Ala Ala Leu Asp Asn Val Lys Thr Ser Leu Pro Thr Asp Phe Pro Glu
                405                 410                 415 aac gtg gtg acg gca gtt gaa agc aat gtg ttg agg ttg cat gga cgg   1296
Asn Val Val Thr Ala Val Glu Ser Asn Val Leu Arg Leu His Gly Arg
            420                 425                 430 tta agc cga gaa tac ggt agt aag tga                               1323
Leu Ser Arg Glu Tyr Gly Ser Lys
```

Leu Ser Arg Glu Tyr Gly Ser Lys
        435                 440

<210> SEQ ID NO 32
<211> LENGTH: 440
<212> TYPE: PRT
<213> ORGANISM: Escherichia coli

<400> SEQUENCE: 32

Met Pro Lys Leu Val Thr Trp Met Asn Asn Gln Arg Val Gly Glu Leu
1               5                   10                  15

Thr Lys Leu Ala Asn Gly Ala His Thr Phe Lys Tyr Ala Pro Glu Trp
            20                  25                  30

Leu Ala Ser Arg Tyr Ala Arg Pro Leu Ser Leu Ser Leu Pro Leu Gln
        35                  40                  45

Arg Gly Asn Ile Thr Ser Asp Ala Val Phe Asn Phe Phe Asp Asn Leu
    50                  55                  60

Leu Pro Asp Ser Pro Ile Val Arg Asp Arg Ile Val Lys Arg Tyr His
65                  70                  75                  80

Ala Lys Ser Arg Gln Pro Phe Asp Leu Leu Ser Glu Ile Gly Arg Asp
                85                  90                  95

Ser Val Gly Ala Val Thr Leu Ile Pro Glu Asp Glu Thr Val Thr His
            100                 105                 110

Pro Ile Met Ala Trp Glu Lys Leu Thr Glu Ala Arg Leu Glu Glu Val
        115                 120                 125

Leu Thr Ala Tyr Lys Ala Asp Ile Pro Leu Gly Met Ile Arg Glu Glu
    130                 135                 140

Asn Asp Phe Arg Ile Ser Val Ala Gly Ala Gln Glu Lys Thr Ala Leu
145                 150                 155                 160

Leu Arg Ile Gly Asn Asp Trp Cys Ile Pro Lys Gly Ile Thr Pro Thr
                165                 170                 175

Thr His Ile Ile Lys Leu Pro Ile Gly Glu Ile Arg Gln Pro Asn Ala
            180                 185                 190

Thr Leu Asp Leu Ser Gln Ser Val Asp Asn Glu Tyr Tyr Cys Leu Leu
        195                 200                 205

Leu Ala Lys Glu Leu Gly Leu Asn Val Pro Asp Ala Glu Ile Ile Lys
    210                 215                 220

Ala Gly Asn Val Arg Ala Leu Ala Val Glu Arg Phe Asp Arg Arg Trp
225                 230                 235                 240

Asn Ala Glu Arg Thr Val Leu Leu Arg Leu Pro Gln Glu Asp Met Cys
                245                 250                 255

Gln Thr Phe Gly Leu Pro Ser Ser Val Lys Tyr Glu Ser Asp Gly Gly
            260                 265                 270

Pro Gly Ile Ala Arg Ile Met Ala Phe Leu Met Gly Ser Ser Glu Ala
        275                 280                 285

Leu Lys Asp Arg Tyr Asp Phe Met Lys Phe Gln Val Phe Gln Trp Leu
    290                 295                 300

Ile Gly Ala Thr Asp Gly His Ala Lys Asn Phe Ser Val Phe Ile Gln
305                 310                 315                 320

Ala Gly Gly Ser Tyr Arg Leu Thr Pro Phe Tyr Asp Ile Ile Ser Ala
                325                 330                 335

Phe Pro Val Leu Gly Gly Thr Gly Ile His Ile Ser Asp Leu Lys Leu
            340                 345                 350

Ala Met Gly Leu Asn Ala Ser Lys Gly Lys Lys Thr Ala Ile Asp Lys
        355                 360                 365

```
Ile Tyr Pro Arg His Phe Leu Ala Thr Ala Lys Val Leu Arg Phe Pro
    370                 375                 380

Glu Val Gln Met His Glu Ile Leu Ser Asp Phe Ala Arg Met Ile Pro
385                 390                 395                 400

Ala Ala Leu Asp Asn Val Lys Thr Ser Leu Pro Thr Asp Phe Pro Glu
                405                 410                 415

Asn Val Val Thr Ala Val Glu Ser Asn Val Leu Arg Leu His Gly Arg
            420                 425                 430

Leu Ser Arg Glu Tyr Gly Ser Lys
        435                 440

<210> SEQ ID NO 33
<211> LENGTH: 120
<212> TYPE: DNA
<213> ORGANISM: Artificial
<220> FEATURE:
<223> OTHER INFORMATION: DNA fragment containing attL

<400> SEQUENCE: 33
agatcttgaa gcctgctttt ttatactaag ttggcattat aaaaaagcat tgcttatcaa    60
tttgttgcaa cgaacaggtc actatcagtc aaaataaaat cattatttga tttcgaattc   120

<210> SEQ ID NO 34
<211> LENGTH: 40
<212> TYPE: DNA
<213> ORGANISM: Artificial
<220> FEATURE:
<223> OTHER INFORMATION: primer P1

<400> SEQUENCE: 34
ctagtaagat cttgaagcct gctttttat actaagttgg                           40

<210> SEQ ID NO 35
<211> LENGTH: 41
<212> TYPE: DNA
<213> ORGANISM: Artificial
<220> FEATURE:
<223> OTHER INFORMATION: primer P2

<400> SEQUENCE: 35
atgatcgaat tcgaaatcaa ataatgattt tattttgact g                        41

<210> SEQ ID NO 36
<211> LENGTH: 184
<212> TYPE: DNA
<213> ORGANISM: Artificial
<220> FEATURE:
<223> OTHER INFORMATION: DNA fragment containing attR

<400> SEQUENCE: 36
ctgcagtctg ttacaggtca ctaataccat ctaagtagtt gattcatagt gactgcatat    60
gttgtgtttt acagtattat gtagtctgtt ttttatgcaa aatctaattt aatatattga   120
tatttatatc attttacgtt tctcgttcag ctttttttata ctaacttgag cgtctagaaa   180
gctt                                                                184

<210> SEQ ID NO 37
<211> LENGTH: 41
<212> TYPE: DNA
<213> ORGANISM: Artificial
<220> FEATURE:
<223> OTHER INFORMATION: primer P3
```

<400> SEQUENCE: 37
atgccactgc agtctgttac aggtcactaa taccatctaa g                41

<210> SEQ ID NO 38
<211> LENGTH: 46
<212> TYPE: DNA
<213> ORGANISM: Artificial
<220> FEATURE:
<223> OTHER INFORMATION: primer P4

<400> SEQUENCE: 38
accgttaagc tttctagacg ctcaagttag tataaaaaag ctgaac           46

<210> SEQ ID NO 39
<211> LENGTH: 38
<212> TYPE: DNA
<213> ORGANISM: Artificial
<220> FEATURE:
<223> OTHER INFORMATION: primer P5

<400> SEQUENCE: 39
ttcttagacg tcaggtggca cttttcgggg aaatgtgc                    38

<210> SEQ ID NO 40
<211> LENGTH: 37
<212> TYPE: DNA
<213> ORGANISM: Artificial
<220> FEATURE:
<223> OTHER INFORMATION: primer P6

<400> SEQUENCE: 40
taacagagat ctcgcgcaga aaaaaggat ctcaaga                      37

<210> SEQ ID NO 41
<211> LENGTH: 46
<212> TYPE: DNA
<213> ORGANISM: Artificial
<220> FEATURE:
<223> OTHER INFORMATION: primer P7

<400> SEQUENCE: 41
aacagagatc taagcttaga tcctttgcct ggcggcagta gcgcgg           46

<210> SEQ ID NO 42
<211> LENGTH: 35
<212> TYPE: DNA
<213> ORGANISM: Artificial
<220> FEATURE:
<223> OTHER INFORMATION: primer P8

<400> SEQUENCE: 42
ataaactgca gcaaaaagag tttgtagaaa cgcaa                       35

<210> SEQ ID NO 43
<211> LENGTH: 1388
<212> TYPE: DNA
<213> ORGANISM: Artificial
<220> FEATURE:
<223> OTHER INFORMATION: DNA fragment containing Tc gene and ter_thrL

<400> SEQUENCE: 43
gaattctcat gtttgacagc ttatcatcga taagctttaa tgcggtagtt tatcacagtt    60
aaattgctaa cgcagtcagg caccgtgtat gaaatctaac aatgcgctca tcgtcatcct   120

```
cggcaccgtc accctggatg ctgtaggcat aggcttggtt atgccggtac tgccgggcct    180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
ccgccgccca gtcctgctcg cttcgctact tggagccact atcgactacg cgatcatggc    360
gaccacaccc gtcctgtgga tcctctacgc cggacgcatc gtggccggca tcaccggcgc    420
cacaggtgcg gttgctggcg cctatatcgc cgacatcacc gatggggaag atcgggctcg    480
ccacttcggg ctcatgagcg cttgtttcgg cgtgggtatg gtggcaggcc ccgtggccgg    540
gggactgttg ggcgccatct ccttgcatgc accattcctt gcggcggcgg tgctcaacgg    600
cctcaaccta ctactgggct gcttcctaat gcaggagtcg cataagggag agcgtcgacc    660
gatgcccttg agagcttca acccagtcag ctccttccgg tgggcgcggg gcatgactat    720
cgtcgccgca cttatgactg tcttctttat catgcaactc gtaggacagg tgccggcagc    780
gctctgggtc attttcggcg aggaccgctt tcgctggagc gcgacgatga tcggcctgtc    840
gcttgcggta ttcggaatct tgcacgccct cgctcaagcc ttcgtcactg gtcccgccac    900
caaacgtttc ggcgagaagc aggccattat cgccggcatg gcggccgacg cgctgggcta    960
cgtcttgctg gcgttcgcga cgcgaggctg gatggccttc cccattatga ttcttctcgc    1020
ttccggcggc atcgggatgc ccgcgttgca ggccatgctg tccaggcagg tagatgacga    1080
ccatcaggga cagcttcaag gatcgctcgc ggctcttacc agcctaactt cgatcactgg    1140
accgctgatc gtcacggcga tttatgccgc ctcggcgagc acatggaacg ggttggcatg    1200
gattgtaggc gccgccctat accttgtctg cctccccgcg ttgcgtcgcg gtgcatggag    1260
ccgggccacc tcgacctgaa tggaagccgg cggcacctcg ctaacggatt caccactcca    1320
actagaaagc ttaacacaga aaaagcccg cacctgacag tgcgggcttt ttttttcgac    1380
cactgcag                                                            1388
```

<210> SEQ ID NO 44
<211> LENGTH: 36
<212> TYPE: DNA
<213> ORGANISM: Artificial
<220> FEATURE:
<223> OTHER INFORMATION: primer P9

<400> SEQUENCE: 44

```
agtaattcta gaaagcttaa cacagaaaaa agcccg                              36
```

<210> SEQ ID NO 45
<211> LENGTH: 43
<212> TYPE: DNA
<213> ORGANISM: Artificial
<220> FEATURE:
<223> OTHER INFORMATION: primer P10

<400> SEQUENCE: 45

```
ctagtaggat ccctgcagtg gtcgaaaaaa aaagcccgca ctg                      43
```

<210> SEQ ID NO 46
<211> LENGTH: 1162
<212> TYPE: DNA
<213> ORGANISM: Artificial
<220> FEATURE:
<223> OTHER INFORMATION: DNA fragment containing Pa2 promoter

<400> SEQUENCE: 46

```
agatctccgg ataagtagac agcctgataa gtcgcacgaa aaacaggtat tgacaacatg    60
```

```
aagtaacatg cagtaagata caaatcgcta ggtaacacta gcagcgtcaa ccgggcgctc    120
tagctagagc caagctagct tggccggatc cgagattttc aggagctaag gaagctaaaa    180
tggagaaaaa aatcactgga tataccaccg ttgatatatc ccaatggcat cgtaaagaac    240
attttgaggc atttcagtca gttgctcaat gtacctataa ccagaccgtt cagctggata    300
ttacggcctt tttaaagacc gtaaagaaaa ataagcacaa gttttatccg gcctttattc    360
acattcttgc ccgcctgatg aatgctcatc cggaattccg tatggcaatg aaagacggtg    420
agctggtgat atgggatagt gttcacccct gttacaccgt tttccatgag caaactgaaa    480
cgttttcatc gctctggagt gaataccacg acgatttccg gcagtttcta cacatatatt    540
cgcaagatgt ggcgtgttac ggtgaaaacc tggcctattt ccctaaaggg tttattgaga    600
atatgttttt cgtctcagcc aatccctggg tgagtttcac cagttttgat ttaaacgtgg    660
ccaatatgga caacttcttc gcccccgttt tcaccatggg caaatattat acgcaaggcg    720
acaaggtgct gatgccgctg gcgattcagg ttcatcatgc cgtctgtgat ggcttccatg    780
tcggcagaat gcttaatgaa ttacaacagt actgcgatga gtggcagggc ggggcgtaat    840 tttttttaagg cagttattgg tgcccttaaa cgcctggtgc tacgcctgaa taagtgataa    900
taagcggatg aatggcagaa attcgtcgaa gcttaacaca gaaaaaagcc cgcacctgac    960
agtgcgggct tttttttttcg accactgcag tctgttacag gtcactaata ccatctaagt   1020
agttgattca tagtgactgc atatgttgtg ttttacagta ttatgtagtc tgttttttat    1080
gcaaaatcta atttaatata ttgatattta tatcatttta cgtttctcgt tcagcttttt   1140
tatactaact tgagcgtcta ga                                             1162

<210> SEQ ID NO 47
<211> LENGTH: 37
<212> TYPE: DNA
<213> ORGANISM: Artificial
<220> FEATURE:
<223> OTHER INFORMATION: primer P11

<400> SEQUENCE: 47
atcgaggtac cagatctccg gataagtaga cagcctg                              37

<210> SEQ ID NO 48
<211> LENGTH: 32
<212> TYPE: DNA
<213> ORGANISM: Artificial
<220> FEATURE:
<223> OTHER INFORMATION: primer P12

<400> SEQUENCE: 48
gaaggtctag agcgcccggt tgacgctgct ag                                   32

<210> SEQ ID NO 49
<211> LENGTH: 27
<212> TYPE: DNA
<213> ORGANISM: Artificial
<220> FEATURE:
<223> OTHER INFORMATION: primer P13

<400> SEQUENCE: 49
ctaatatcga tgaagattct tgctcaa                                         27

<210> SEQ ID NO 50
<211> LENGTH: 34
<212> TYPE: DNA
```

```
<213> ORGANISM: Artificial
<220> FEATURE:
<223> OTHER INFORMATION: primer P14

<400> SEQUENCE: 50
gcgttgaatt ccatacaacc tccttagtac atgc                                34

<210> SEQ ID NO 51
<211> LENGTH: 34
<212> TYPE: DNA
<213> ORGANISM: Artificial
<220> FEATURE:
<223> OTHER INFORMATION: primer P15

<400> SEQUENCE: 51
gtactagaat tcgtgtaatt gcggagactt tgcg                                34

<210> SEQ ID NO 52
<211> LENGTH: 41
<212> TYPE: DNA
<213> ORGANISM: Artificial
<220> FEATURE:
<223> OTHER INFORMATION: primer P16

<400> SEQUENCE: 52
aatagcctgc agttatttga tttcaattttt gtcccactcc c                       41

<210> SEQ ID NO 53
<211> LENGTH: 60
<212> TYPE: DNA
<213> ORGANISM: Artificial
<220> FEATURE:
<223> OTHER INFORMATION: primer P17

<400> SEQUENCE: 53
tcacttacta ccgtattctc ggcttaaccg tccatgtgaa gcctgctttt ttatactaag    60

<210> SEQ ID NO 54
<211> LENGTH: 59
<212> TYPE: DNA
<213> ORGANISM: Artificial
<220> FEATURE:
<223> OTHER INFORMATION: primer P18

<400> SEQUENCE: 54
atgcctaaac ttgtcacttg gatgaacaac cagcgcgctc aagttagtat aaaaaagct     59

<210> SEQ ID NO 55
<211> LENGTH: 19
<212> TYPE: DNA
<213> ORGANISM: Artificial
<220> FEATURE:
<223> OTHER INFORMATION: primer P19

<400> SEQUENCE: 55
acaataccac gctcacgac                                                 19

<210> SEQ ID NO 56
<211> LENGTH: 19
<212> TYPE: DNA
<213> ORGANISM: Artificial
<220> FEATURE:
<223> OTHER INFORMATION: primer P20

<400> SEQUENCE: 56
ttcgcatcac tcagacatg                                                 19
```

```
<210> SEQ ID NO 57
<211> LENGTH: 19
<212> TYPE: DNA
<213> ORGANISM: Artificial
<220> FEATURE:
<223> OTHER INFORMATION: primer P21

<400> SEQUENCE: 57
agctacctct ctctgattc                                                    19

<210> SEQ ID NO 58
<211> LENGTH: 19
<212> TYPE: DNA
<213> ORGANISM: Artificial
<220> FEATURE:
<223> OTHER INFORMATION: primer P22

<400> SEQUENCE: 58
tgtttcccat agcatcctc                                                    19
```

METHOD FOR PRODUCING AN L-AMINO ACID USING A BACTERIUM OF THE *ENTEROBACTERIACEAE* FAMILY BY INACTIVATING A GENE ENCODING A TOXIN OF A BACTERIAL TOXIN-ANTITOXIN PAIR

This application claims priority under 35 U.S.C. §119 to Russian Patent Application No. 2005104462, filed on Feb. 18, 2005, Russian Patent Application No. 2005104461, filed on Feb. 18, 2005, Russian Patent Application No. 2005104460, filed on Feb. 18, 2005, Russian Patent Application No. 2005106344, filed on Mar. 10, 2005, Russian Patent Application No. 2005109258, filed on Mar. 31, 2005, Russian Patent Application No. 2005125291, filed on Aug. 9, 2005, U.S. Provisional Patent Application No. 60/714,848, filed on Aug. 9, 2005, U.S. Provisional Patent Application No. 60/714,844, filed on Sep. 8, 2005, U.S. Provisional Patent Application No. 60/714,849, filed on Sep. 8, 2005, and U.S. Provisional Patent Application No. 60/723,929, filed on Oct. 6, 2005, and under 35 U.S.C. §120 as a continuation to PCT/JP2006/303215, filed Feb. 16, 2006, the contents of all of which are incorporated by reference in their entireties. The Sequence Listing filed electronically herewith is also hereby incorporated by reference in its entirety (File Name: US-205_Seq_List_Copy__1; File Size: 34 KB; Date Created: Jul. 31, 2007).

BACKGROUND OF THE INVENTION

1. Field of the Invention

The present invention relates to the microbiological industry, and specifically to a method for producing an L-amino acid using a bacterium of the Enterobacteriaceae family.

2. Brief Description of the Related Art

Bacterial toxin-antitoxin pairs are typically made up of a stable toxin protein that can cause cell death by disrupting an essential cellular process, coupled with a labile antitoxin protein that can bind to and block activity of the toxin.

YoeB and YefM are a known toxin-antitoxin pair. The YoeB protein is similar to the Txe protein and the YefM protein is similar to the Axe protein. Both the Txe-Axe toxin-antitoxin pair are encoded by a multidrug resistance episome isolated from *Enterococcus faecium* (Grady, R. and Hayes, F., Mol. Microbiol., 47(5); 1419-32 (2003)). YoeB recognizes and binds to a linear peptide sequence within YefM (Cherny, I. and Gazit, E., J. Biol. Chem. 279(9); 8252-61 (2004)). The YoeB toxin induces cleavage of translated mRNAs. YoeB can be activated by overproduction of the Lon protease, which is lethal for bacterial cells (Christensen S. K. et al, Mol. Microbiol., 51(6); 1705-17 (2004)). The YefM protein appears to lack secondary structure, and its native conformation is proposed to be unfolded. A linear recognition element which is recognized by YoeB was identified using peptide array technology (Cherny, I. and Gazit, E., J. Biol. Chem. 279(9); 8252-61 (2004)).

YafQ and DinJ are another known toxin-antitoxin pair, with DinJ (DNA damage inducible protein) being the antitoxin for the YafQ protein (Gerdes, K., J. Bacteriol., 182(3): 561-72 (2000); Christensen S. K. et al, Mol. Microbiol., 51(6); 1705-17 (2004)). It was shown that under the stringent conditions of growth arrest, the YafQ and DinJ pair is significantly upregulated along with several other toxin-antitoxin pairs (Chang, D. E. et al, Mol. Microbiol., 45(2): 289-306 (2002)).

The mazEF system encodes the MazE-MazF toxin-antitoxin pair, with MazF being the toxin that is counteracted by the MazE antitoxin (Aizenman, E. et al, Proc. Natl. Acad. Sci. USA, 93 (12); 6059-63 (1996)). The MazE-MazF system mediates the toxicity of guanosine 3',5'-bispyrophosphate (rapid relA induction), which is associated with amino acid deprivation (Aizenman, E. et al, Proc. Natl. Acad. Sci. USA, 93 (12); 6059-63 (1996)); cell death caused by the antibiotics rifampicin, chloramphenicol, and spectinomycin (Sat, B. et al, J. Bacteriol., 183(6); 2041-5 (2001)); and the thymineless death (TLD) response to thymine starvation (Sat, B. et al, J. Bacteriol., 185(6); 1803-7 (2003)). The MazE antitoxin is subject to degradation by the ClpP-ClpA protease complex and exhibits a short (30 minute) half life, whereas the toxin, MazF, is much more stable. It has been shown that overproduction of MazE has no effect on the absence of MazF (Aizenman, E. et al, Proc. Natl. Acad. Sci. USA, 93 (12); 6059-63 (1996)). MazF exhibits sequence-specific ribonuclease activity toward single- or double-stranded RNA regions (Munoz-Gomez, et al, FEBS Lett., 567(2-3); 316-20 (2004)), and the resulting degradation of cellular MRNA causes global translation inhibition (Zhang, Y. et al, Mol. Cell, 12(4); 913-23 (2003)). MazF exhibits RNase activity toward tmRNA, and tmRNA is involved in the release of MazF-mediated cell growth inhibition (Christensen, S. K. et al, J. Mol. Biol., 332(4); 809-19 (2003)). MazF also stimulates DNA binding by MazE (Zhang, J. et al, J. Biol. Chem. 278(34); 32300-6 (2003)).

RelE is the toxin in the RelE-RelB toxin-antitoxin system (Gotfredsen, M. and Gerdes, K., Mol. Microbiol. 29(4), 1065-76 (1998)). RelE and RelB proteins exhibit a physical interaction, and the RelE protein physically interacts with ribosomes (Galvani, C. et al, J. Bacteriol., 183(8), 2700-3 (2001)). RelE inhibits protein translation by catalyzing cleavage of mRNA in the A site of the ribosome (Pedersen, K. et al, Cell 112(1), 131-40 (2003)). RelE is involved in regulation of cellular protein translation when nutrients are limited (Christensen, S. K. et al, Proc. Natl. Acad. Sci. USA, 98(25), 14328-33 (2001); Pedersen, K. et al, Cell 112(1), 131-40 (2003); Christensen, S. K. and Gerdes, K., Mol. Microbiol., 48(5), 1389-400 (2003)). When cells are starved of amino acids, Lon protease degrades RelB protein; degradation of RelB protein derepresses transcription of relBE operon; RelE toxin accumulates in excess compared with its RelB antitoxin; and this free RelE toxin causes translation inhibition (Christensen, S. K. et al, Proc. Natl. Acad. Sci. USA, 98(25), 14328-33 (2001). RelE-mediated translation inhibition is reported to cause reversible inhibition of cell growth (Pedersen, K. et al, Mol. Microbiol., 45(2); 501-10 (2002)).

YeeV is a member of novel family of toxin proteins, ectopic expression of which caused growth inhibition. Coexpression of the gene upstream of each of these toxins restored the growth rate to that of the uninduced strain (Brown, J. M. and Shaw, K. J., J. Bacteriol., 185 (22), 6600-6608 (2003)).

The ability of *Escherichia coli* cells to survive prolonged exposure to penicillin antibiotics, called high persistence (hip), is associated with mutations in the hipA gene. The hip operon consists of two genes, hipA and hipB. The hipA gene encodes the HipA toxin, whereas hipB encodes a DNA-binding protein that autoregulates expression of the hipBA operon and binds to HipA to nullify its toxic effects (Korch, S. B., Henderson, T. A., and Hill, T. M., Mol. Microbiol., 2003, 50(4):1199-1213). Bacterial populations produce persisters, cells that neither grow nor die in the presence of bactericidal agents, and thus exhibit multidrug tolerance (MDT). Deletion of the hipBA operon causes a sharp decrease in persisters in both stationary and biofilm populations. The hipA gene is thus the first validated persister-MDT gene (Keren, I. et al., J. Bacteriol., 2004, 186(24):8172-8180). It has been shown that mutations in the hipA gene of *Escherichia coli* K-12 greatly reduce the lethality of selective inhibition of peptidoglycan synthesis. These mutations reduce the lethality that accompanies either selective inhibition of DNA synthesis or heat shock of strains defective in htpR. In addition, the mutant alleles of hipA are responsible for a reversible cold-sensitive block in cell division and synthesis of macromolecules, particularly peptidoglycan (Scherrer, R. and Moyed, H. S., J. Bacteriol., 1988, 170(8):3321-3326). It has also been shown that overexpression of hipA produces an antibiotic tolerance phenotype under conditions that do not affect the growth rate of the organism. Overexpressing hipA probably decreases the period in which bacteria are susceptible to the antibiotics by temporarily affecting some aspect of chromosome replication or cell division (Falla, T. J. and Chopra I., Antimicrob Agents Chemother., 1998, 42(12):3282-3284).

But currently, there have been no reports of attenuation of expression of a gene encoding a toxin of bacterial toxin-antitoxin pairs for the purpose of producing of L-amino acids.

SUMMARY OF THE INVENTION

Objects of the present invention include enhancing the productivity of L-amino acid producing strains and providing a method for producing an L-amino acid using these strains.

The above objects were achieved by finding that attenuating expression of a gene encoding a toxin of a bacterial toxin-antitoxin pair can enhance production of L-amino acids, such as L-threonine, L-lysine, L-cysteine, L-leucine, L-histidine, L-glutamic acid, L-phenylalanine, L-tryptophan, L-proline, and L-arginine.

The present invention provides a bacterium of the Enterobacteriaceae family having an increased ability to produce amino acids, such as L-threonine, L-lysine, L-cysteine, L-leucine, L-histidine, L-glutamic acid, L-phenylalanine, L-tryptophan, L-proline, and L-arginine.

It is an object of the present invention to provide an L-amino acid producing bacterium of the Enterobacteriaceae family, wherein the bacterium has been modified to attenuate expression of a gene encoding a toxin of a bacterial toxin-antitoxin pair.

It is a further object of the present invention to provide the bacterium as described above, wherein the expression of a gene encoding a toxin of a bacterial toxin-antitoxin pair is attenuated by inactivation of the gene.

It is a further object of the present invention to provide the bacterium as described above, wherein the gene is selected from the group consisting of yoeB, yafQ, mazF, relE, yeeV, and hipA.

It is a further object of the present invention to provide the bacterium as described above, wherein the bacterium belongs to the genus *Escherichia*.

It is a further object of the present invention to provide the bacterium as described above, wherein the bacterium belongs to the genus *Pantoea*.

It is a further object of the present invention to provide the bacterium as described above, wherein said L-amino acid is selected from the group consisting of an aromatic L-amino acid and a non-aromatic L-amino acid.

It is a further object of the present invention to provide the bacterium as described above, wherein said aromatic L-amino acid is selected from the group consisting of L-phenylalanine, L-tyrosine, and L-tryptophan.

It is a further object of the present invention to provide the bacterium as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

It is a further object of the present invention to provide a method for producing an L-amino acid comprising:
 cultivating the bacterium as described above in a medium to produce and excrete said L-amino acid into the medium, and
 collecting said L-amino acid from the medium.

It is a further object of the present invention to provide the method as described above, wherein said L-amino acid is selected from the group consisting of an aromatic L-amino acid and a non-aromatic L-amino acid.

It is a further object of the present invention to provide the method as described above, wherein said aromatic L-amino acid is selected from the group consisting of L-phenylalanine, L-tyrosine, and L-tryptophan.

It is a further object of the present invention to provide the method as described above, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine.

The present invention is described in detail below.

DESCRIPTION OF THE PREFERRED EMBODIMENTS

1. Bacterium of the Present Invention

Figure 1:
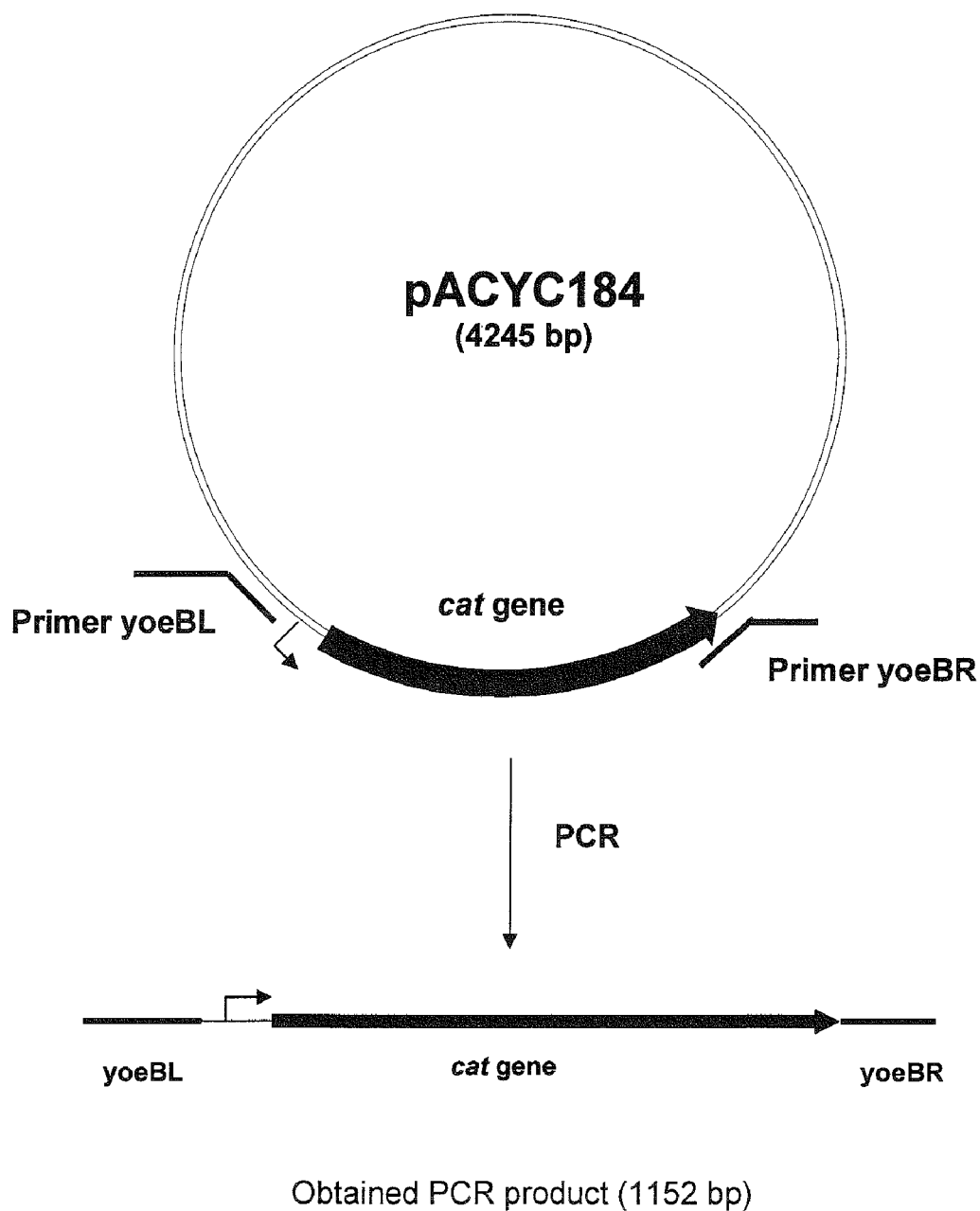
FIG. 1 shows the relative positions of primers yoeBL and yoeBR on plasmid pACYC184, which is used for amplification of the cat gene.
Figure 2:
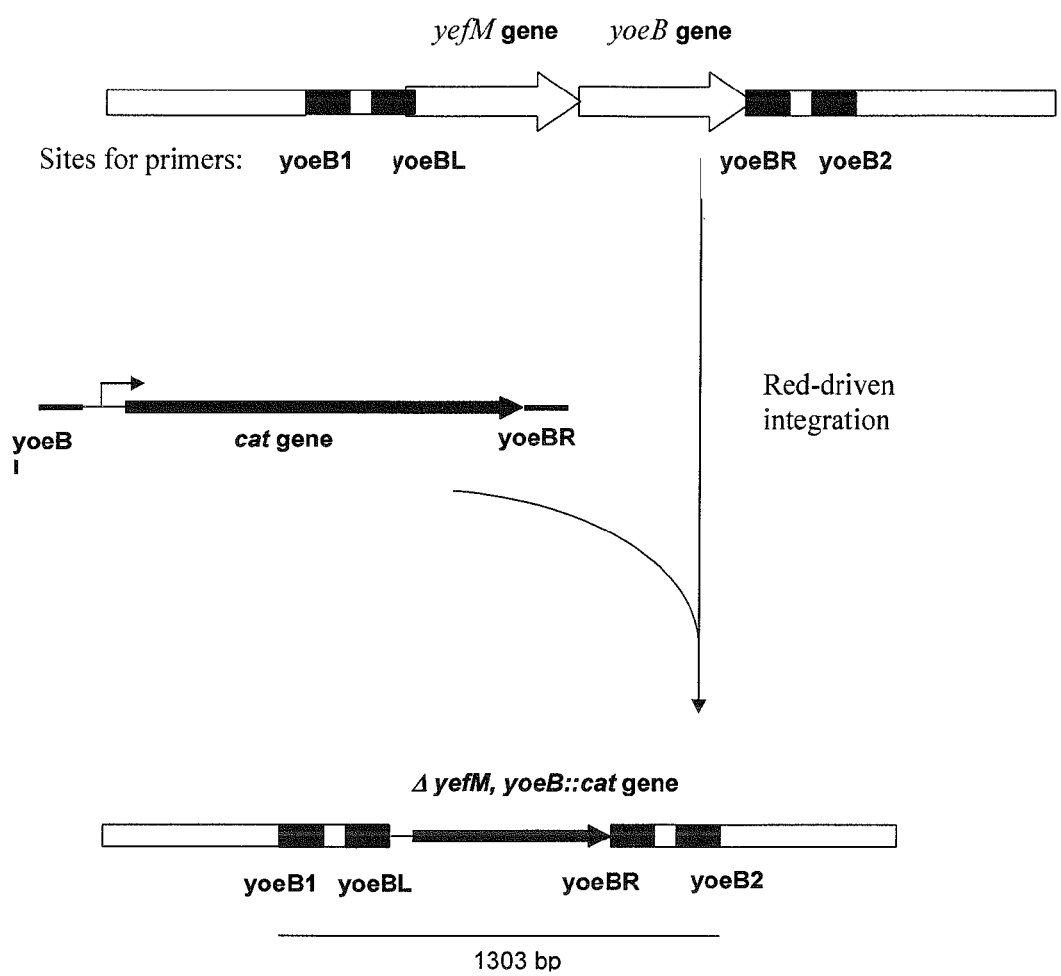
FIG. 2 shows the construction of the chromosomal DNA fragment containing the inactivated yefM-yoeB operon.
Figure 3:
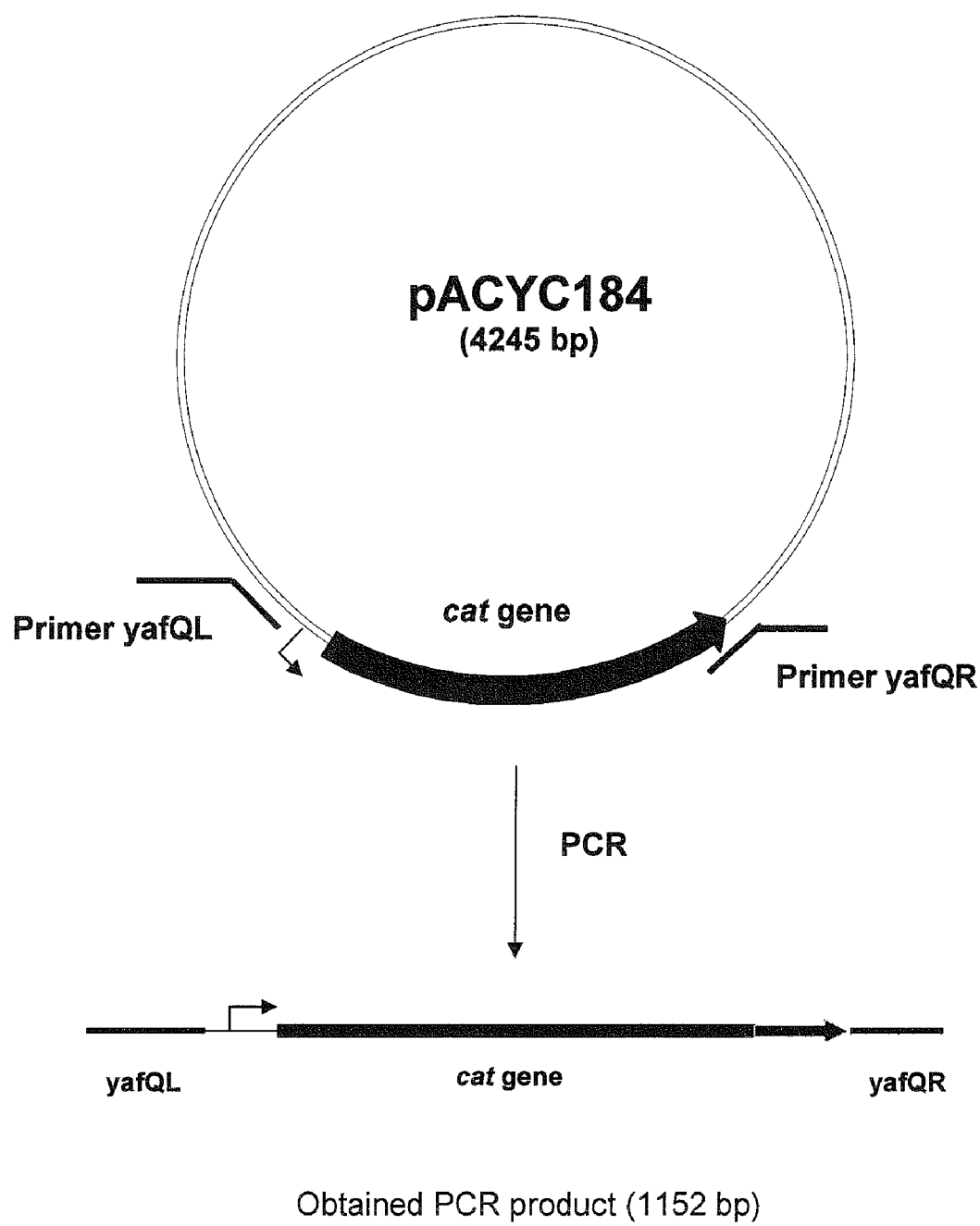
FIG. 3 shows the relative positions of primers yafQL and yafQR on plasmid pACYC184, which is used for amplification of the cat gene.
Figure 4:
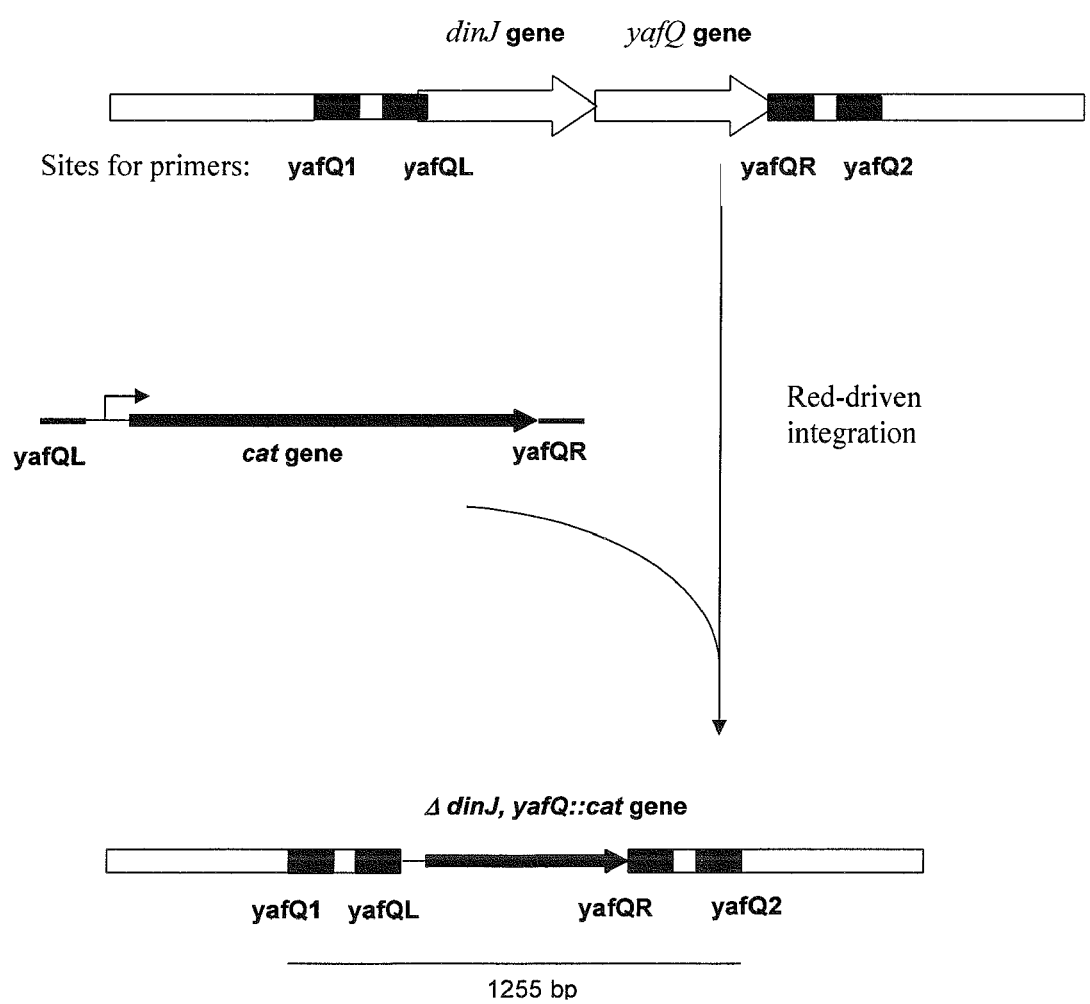
FIG. 4 shows the construction of the chromosomal DNA fragment containing the inactivated dinJ-yafQ operon.
Figure 5:
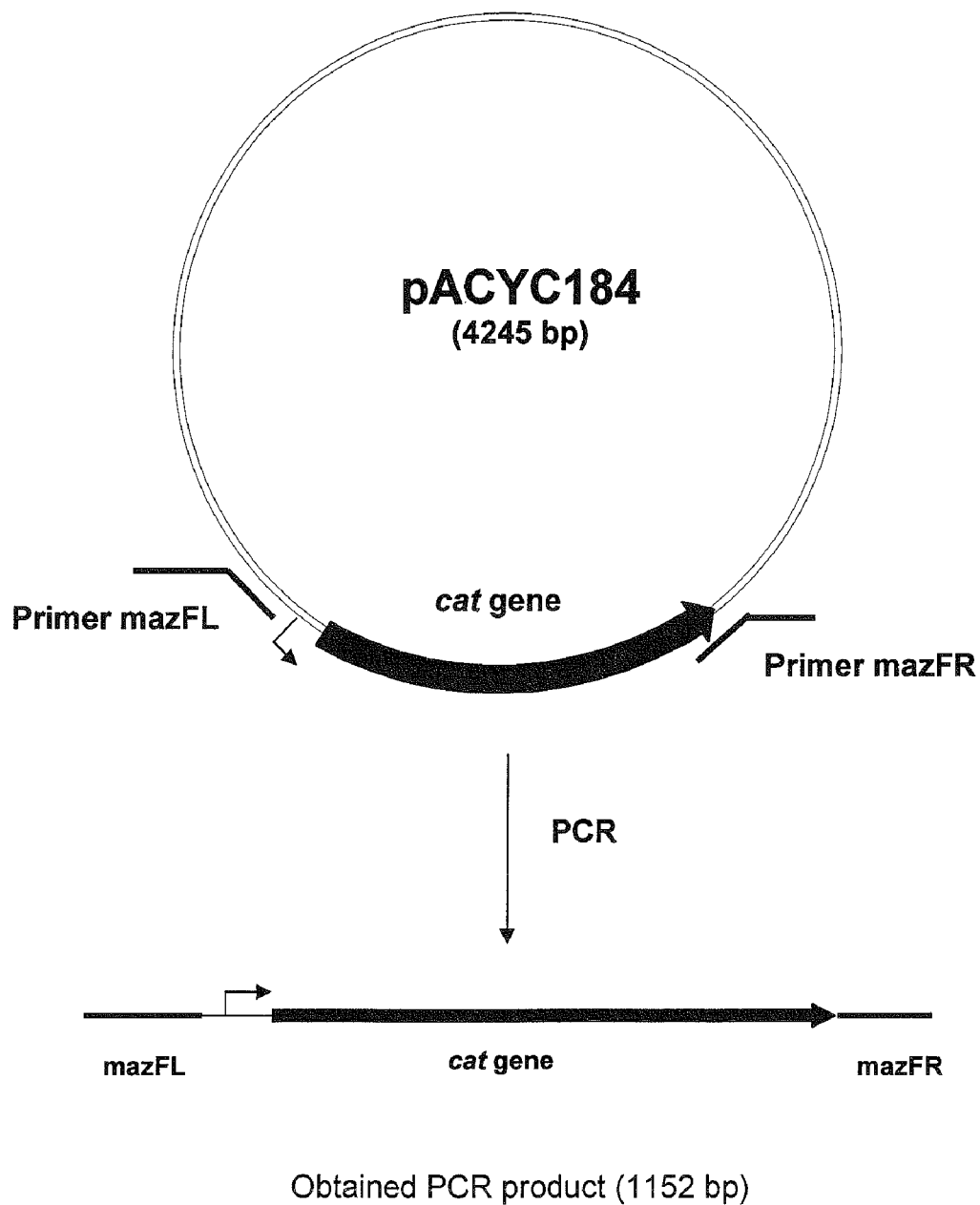
FIG. 5 shows the relative positions of primers mazFL and mazFR on plasmid pACYC184, which is used for amplification of the cat gene.
Figure 6:
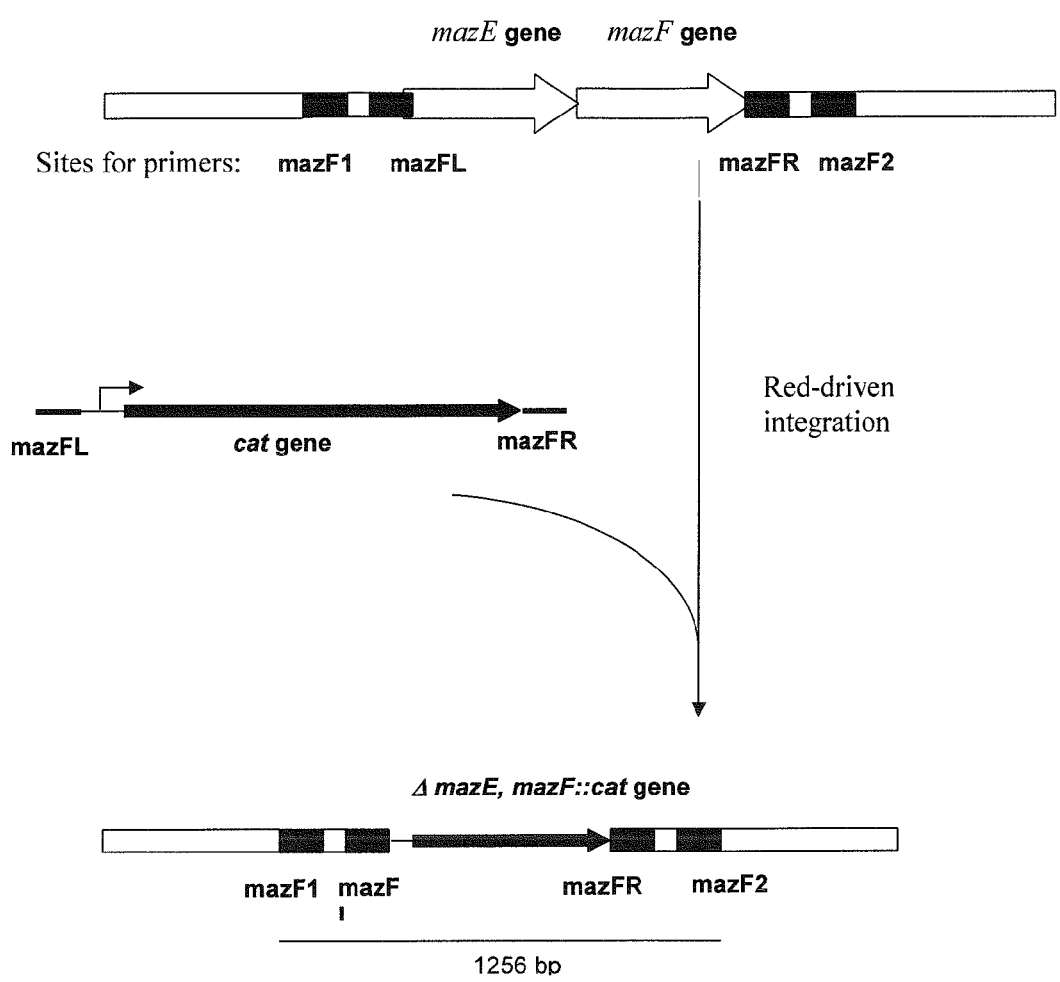
FIG. 6 shows the construction of the chromosomal DNA fragment containing the inactivated mazEF operon.
Figure 7:
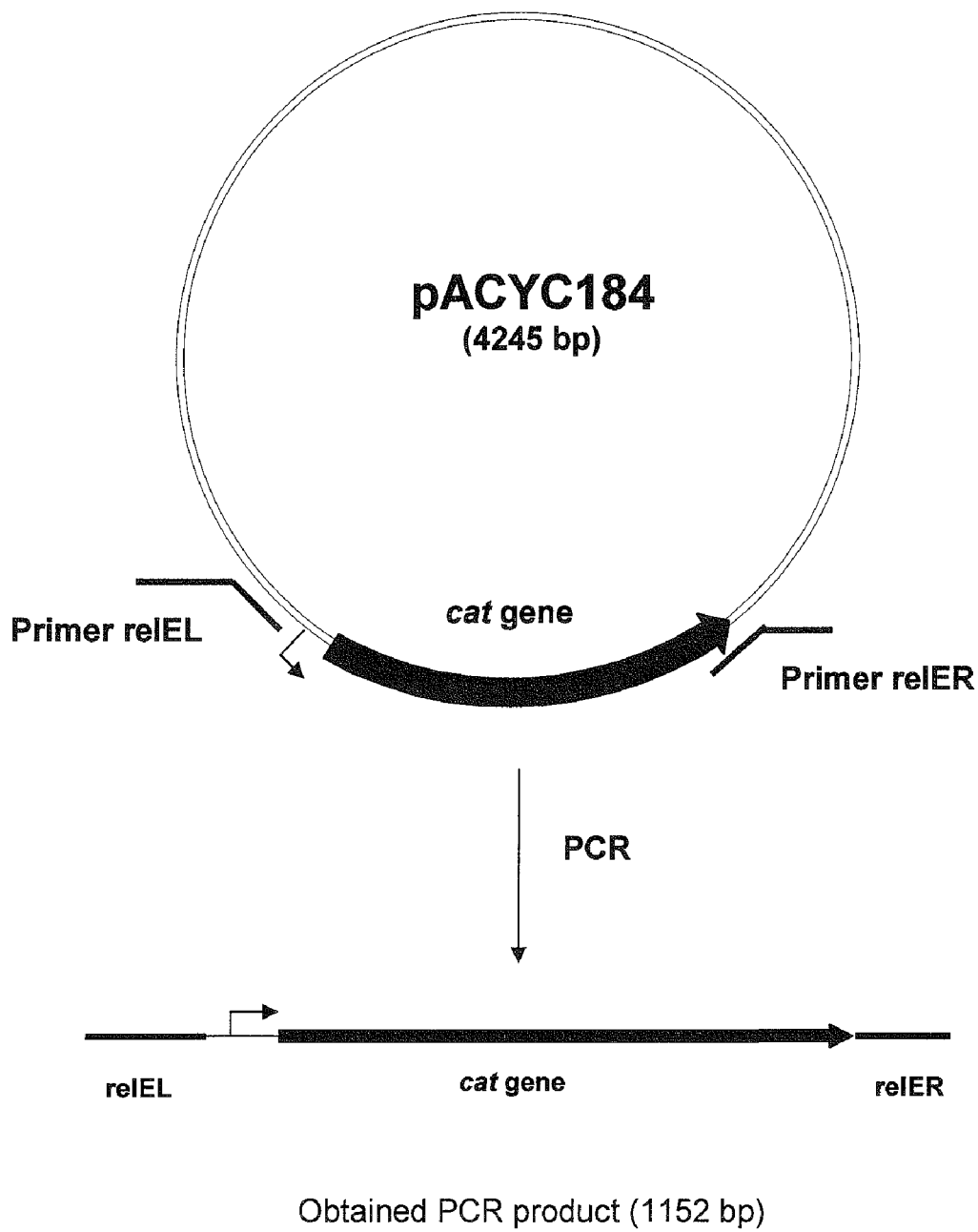
FIG. 7 shows the relative positions of primers relEL and relER on plasmid pACYC184, which is used for amplification of the cat gene.
Figure 8:
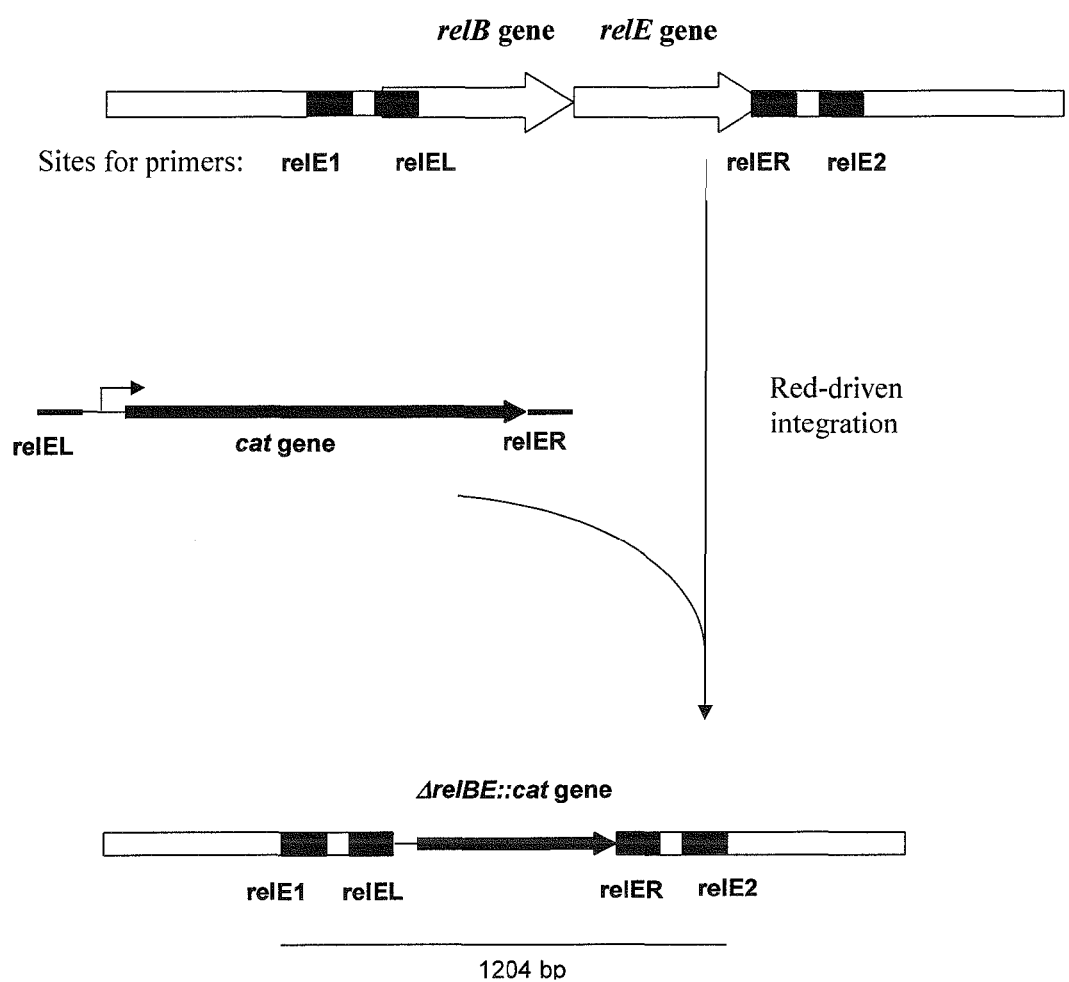
FIG. 8 shows the construction of the chromosomal DNA fragment containing the inactivated relBE operon.
Figure 9:
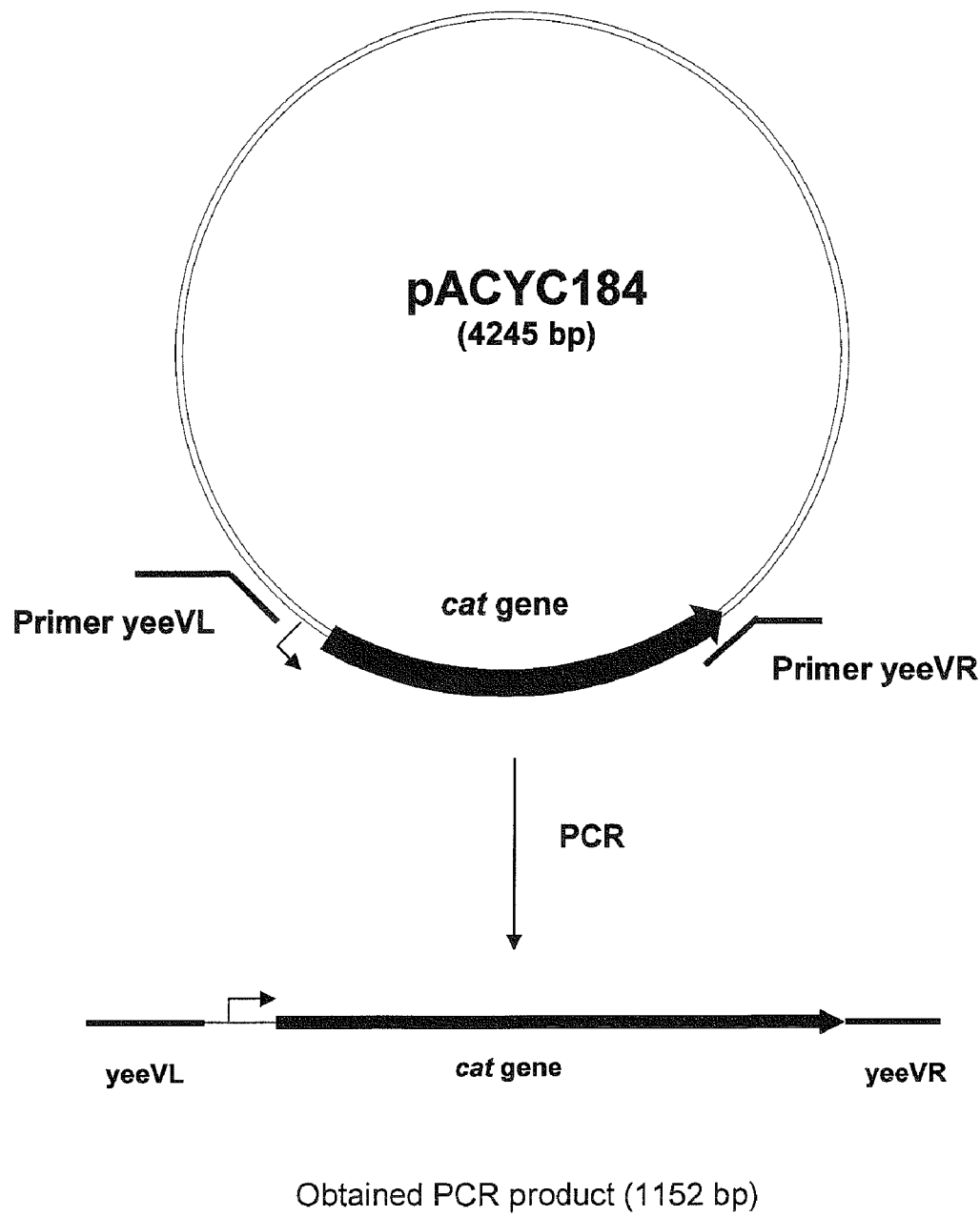
FIG. 9 shows the relative positions of primers yeeVL and yeeVR on plasmid pACYC184, which is used for amplification of the cat gene.
Figure 10:
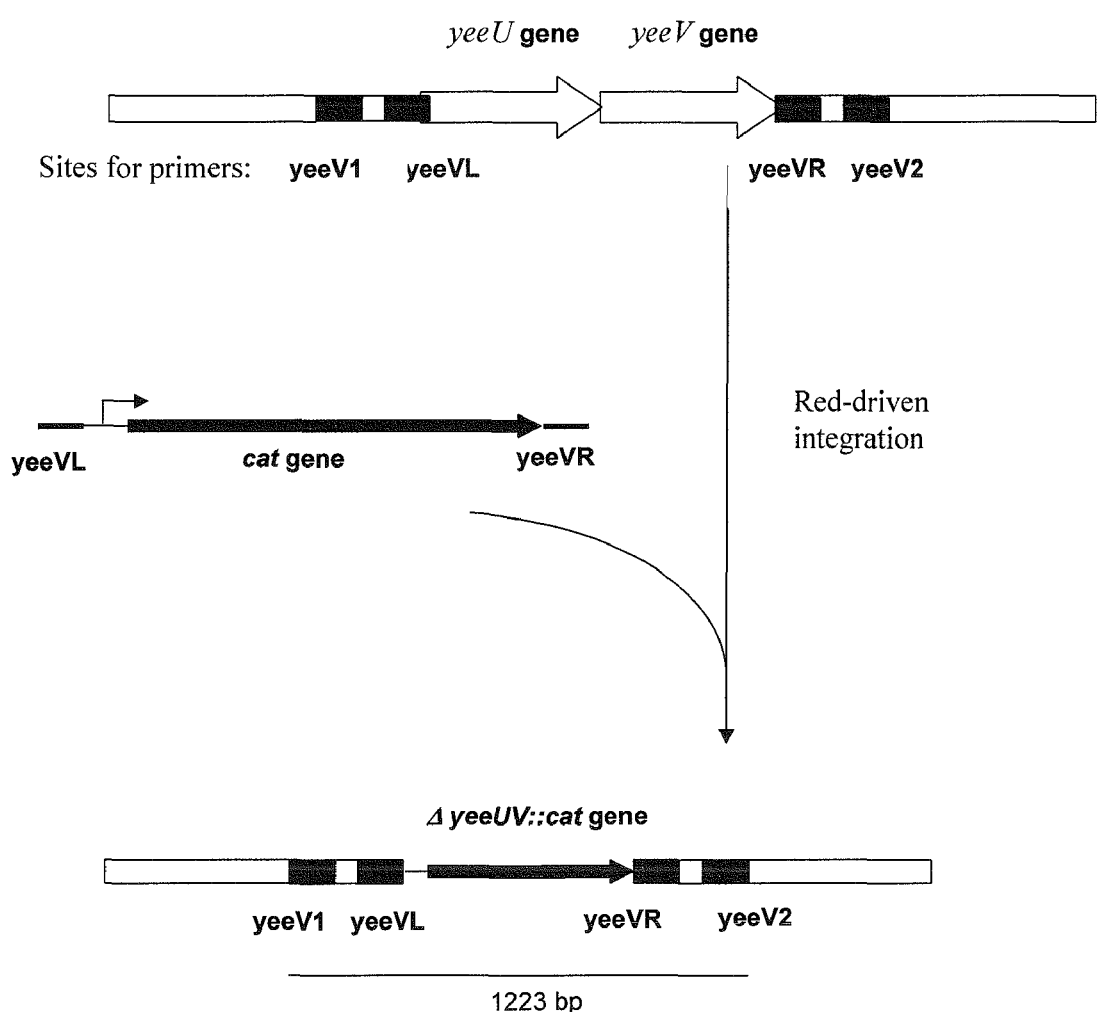
FIG. 10 shows the construction of the chromosomal DNA fragment containing the inactivated yeeUV operon.

The bacterium of the present invention is an L-amino acid producing bacterium of the Enterobacteriaceae family, wherein the bacterium has been modified to attenuate expression of a gene encoding a toxin of a bacterial toxin-antitoxin pair. Preferably, the gene is one of the yoeB, yafQ, mazF, relE, yeeV, and hipA genes.

In the present invention, "L-amino acid producing bacterium" means a bacterium which has an ability to produce and excrete an L-amino acid into a medium, when the bacterium is cultured in the medium.

The phrase "L-amino acid-producing bacterium" as used herein also means a bacterium which is able to produce and cause accumulation of an L-amino acid in a culture medium in an amount larger than a wild-type or parental strain of E. coli, such as E. coli K-12, and preferably means that the microorganism is able to cause accumulation in a medium of an amount not less than 0.5 g/L, more preferably not less than 1.0 g/L of the target L-amino acid. The term "L-amino acids" includes L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-cryptophan, L-tyrosine, and L-valine.

The term "aromatic L-amino acid" includes L-phenylalanine, L-tyrosine, and L-tryptophan. The term "non-aromatic L-amino acid" includes L-threonine, L-lysine, L-cysteine, L-methionine, L-leucine, L-isoleucine, L-valine, L-histidine, L-glycine, L-serine, L-alanine, L-asparagine, L-aspartic acid, L-glutamine, L-glutamic acid, L-proline, and L-arginine. L-threonine, L-lysine, L-cysteine, L-leucine, L-histidine, L-glutamic acid, L-phenylalanine, L-tryptophan, L-proline, and L-arginine are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella Yersinia*, etc. Specifically, those classified into the Enterobacteriaceae according to the taxonomy used in the NCBI (National Center for Biotechnology Information) database can be used. A bacterium belonging to the genus of *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* as used in the present invention include, but are not limited to, *Escherichia coli (E. coli)*.

The bacterium belonging to the genus *Escherichia* that can be used in the present invention is not particularly limited, however for example, bacteria described by Neidhardt, F. C. et al. (*Escherichia coli* and *Salmonella typhimurium*, American Society for Microbiology, Washington D.C., 1208, Table 1) are encompassed by the present invention.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on nucleotide sequence analysis of 16S rRNA, etc. (Int. J. Syst. Bacteriol., 43, 162-173 (1993)).

Bacterial toxin-antitoxin pairs typically include a toxin protein, which poisons cells by binding and inhibiting an essential enzyme, and an antitoxin protein, which binds the toxin and restores viability. The phrase "bacterium has been modified to attenuate expression of a gene encoding a toxin of a bacterial toxin-antitoxin pair" means that the bacterium has been modified in such a way that the modified bacterium has a reduced amount of the toxin encoded by the gene as compared with an unmodified bacterium, or the modified bacterium is unable to synthesize the toxin. The phrase "bacterium has been modified to attenuate expression of a gene encoding a toxin of a bacterial toxin-antitoxin pair" also means that the target gene is modified in such a way that the modified gene encodes a mutant toxin which has a decreased activity.

Preferred examples of the gene encoding a toxin of a bacterial toxin-antitoxin pair include the yoeB, yafQ, mazF, relE, yeeV, and hipA genes. Since the YefM, DinJ, MazE, RelB, YeeU, and HipB proteins function as antitoxins for the YoeB, YafQ, MazF, RelE, YeeV, and HipA toxins, respectively, it is possible to inactivate both of the yefM and yoeB genes, the dinJ and yafQ genes, the mazE and mazF genes, the relB and relE genes, the yeeV and yeeU genes, and the hipA and hipB genes, respectively, in the bacterium according to the present invention.

The phrase "inactivation of a gene encoding a toxin of a bacterial toxin-antitoxin pair" means that the modified gene encodes a completely inactive protein(s). It is also possible that the modified DNA region is unable to naturally express the gene(s) due to the deletion of a part of the gene(s), the shifting of the reading frame of the gene(s), the introduction of missense/nonsense mutation(s), or the modification of an adjacent region of the gene(s), including sequences controlling gene expression, such as promoter(s), enhancer(s), attenuator(s), ribosome-binding site(s), etc.

The yoeB gene encodes the YoeB toxin protein. The yefM gene encodes the YefM antitoxin protein (synonym—B2017). Both the yoeB and yefM genes are located in the yefM-yoeB operon in *E. coli*. The yefM-yoeB operon (nucleotides complementary to nucleotides 2087764 to 2087486 and 2087489 to 2087235 for the yefM and yoeB genes, respectively, in the GenBank accession number NC_000913.2; gi: 49175990) is located between the yeeZ ORF and the gene coding for the histidine operon leader peptide on the chromosome of *E. coli* K-12. The nucleotide sequence of the yoeB gene and the amino acid sequence of the peptide encoded by the yoeB gene are shown in SEQ ID NO: 1 and SEQ ID NO: 2, respectively.

The yafQ gene encodes the YafQ toxin protein (synonym—b0225). The dinJ gene encodes the DinJ antitoxin protein (synonym—b0226). Both the yafQ and dinJ genes are located in the dinJ-yafQ operon in *E. coli*. The dinJ-yafQ operon (nucleotides complementary to nucleotides 246242 to 246502 and 245961 to 246239 for the dinJ and yafQ genes, respectively, in the GenBank accession number NC_000913.2; gi: 49175990) is located between the yafK and yafL ORFs on the chromosome of *E. coli* K-12. The nucleotide sequence of the yafQ gene and the amino acid sequence of the peptide encoded by the yafQ gene are shown in SEQ ID NO: 7 and SEQ ID NO: 8, respectively.

The mazF gene encodes the MazF toxin protein (synonyms—b2782, ChpA, ChpAK). The mazE gene encodes the MazE antitoxin protein (synonyms—b2783, ChpR, ChpAI). Both the mazF and mazE genes are located in the mazEF operon in *E. col*. The mazEF operon (nucleotides complementary to nucleotides 2909113 to 2909361 and 2908778 to 2909113 for mazE and mazF genes, respectively, in the GenBank accession number NC_000913.2; gi: 49175990) is located between the mazG and relA genes on the chromosome of *E. coli* K-12. The nucleotide sequence of the mazF gene and the amino acid sequence of the peptide encoded by the mazF gene are shown in SEQ ID NO: 13 and SEQ ID NO: 14, respectively.

The relE gene encodes the RelE toxin protein (synonym—b1563). The relB gene encodes the RelB antitoxin protein (synonym—b1564). Both the relE and relB genes are located in the relBE operon in *E. coli*. The relBE operon (nucleotides complementary to nucleotides 1643370 to 1643657 and 1643657 to 1643896 for the relE and relB genes, respectively, in the GenBank accession number NC_000913.2; gi:49175990) is located between the hokD (relF) gene and the b1565 putative ORF on the chromosome of *E. coli* K-12. The nucleotide sequence of the relE gene and the amino acid sequence of RelE encoded by the relE gene are shown in SEQ ID NO: 19 and SEQ ID NO: 20, respectively.

The yeeV gene encodes the YeeV toxin protein (synonym—B2005). The yeeU gene encodes the YeeU antitoxin protein (synonym—B2004). Both the yoeB and yefM genes are located in the yeeUV operon. The yeeUV operon (nucleotides 2075136 to 2075504 and 2075593 to 2075967 for the yeeU and yeeV genes, respectively, in the GenBank accession number NC_000913.2; gi: 49175990) is located between the yeeT and yeeW ORFs on the chromosome of *E. coli* K-12. The nucleotide sequence of the yeeV gene and the amino acid sequence of the peptide encoded by the yeeV gene are shown in SEQ ID NO: 25 and SEQ ID NO: 26, respectively.

The hipA gene encodes the HipA protein, a toxin (synonyms—b1507, G7995). The hipA gene (nucleotide positions 1,590,200 to 1,588,878; GenBank accession no. NC_000913.2; gi:49175990) is located between the yneL and hipB genes on the chromosome of *E. coli* K-12. The nucleotide sequence of the hipA gene and the amino acid sequence of the HipA protein encoded by the hipA gene are shown in SEQ ID NO: 31 and SEQ ID NO: 32, respectively.

Since there may be some differences in DNA sequences between the genera or strains of the Enterobacteriaceae family, the gene to be inactivated on the chromosome is not limited to the genes shown in SEQ ID No: 1, 7, 13, 19, 25, or 31, but may include homologous genes to SEQ ID No: 1, 7, 13, 19, 25, or 31 encoding variant proteins of the YoeB, YafQ, MazF, RelE, YeeV, or HipA protein, respectively. The phrase "variant protein" as used in the present invention means a protein which has changes in the sequence, whether they are deletions, insertions, additions, or substitutions of amino acids, but still maintains the activity of the protein product The number of changes in the variant protein depends on the position or the type of amino acid residues in the three dimensional structure of the protein. It may be 1 to 30, preferably 1 to 15, and more preferably 1 to 5 in SEQ ID NO: 2, 8, 14, 20, 26, or 32. These changes in the variants can occur in regions of each protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant encoded by the gene may have a homology of not less than 80%, preferably not less than 90%, and most preferably not less than 95%, with respect to the entire amino acid sequence shown in SEQ ID NO: 2, 8, 14, 20, 26, or 32, as long as the activity of the toxin protein prior to inactivation is maintained.

Homology between two amino acid sequences can be determined using the well-known methods, for example, the computer program BLAST 2.0, which calculates three parameters: score, identity and similarity.

Moreover, the gene to be inactivated may be a variant which hybridizes under stringent conditions with the nucleotide sequence shown in SEQ ID NO: 1, 7, 13, 19, 25, or 31, or a probe which can be prepared from the nucleotide sequence, provided that it encodes a toxin protein prior to inactivation. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration corresponding to 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected depending on the hybridization conditions, and is usually 100 bp to 1 kbp.

Expression of the yoeB, yafQ, mazF, relE, yeeV, and hipA genes can be attenuated by introducing a mutation into the gene on the chromosome so that intracellular activity of the protein encoded by the gene is decreased as compared with an unmodified strain. Such a mutation on the gene can be replacement of one base or more to cause amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (J. Biol. Chem., 1997, 272 (13): 8611-8617, J. Antimicrobial Chemotherapy, 2000, 46: 793-79). Expression of the yoeB, yafQ, mazF, relE, yeeV, and hipA genes can also be attenuated by modifying an expression regulating sequence such as the promoter, the Shine-Dalgarno (SD) sequence, etc. (WO95/34672, Biotechnol. Prog. 1999, 15, 58-64) of these genes.

For example, the following methods may be employed to introduce a mutation by gene recombination. A mutant gene encoding a mutant protein having a decreased activity is prepared, and a bacterium to be modified is transformed with a DNA fragment containing the mutant gene. Then the native gene on the chromosome is replaced with the mutant gene by homologous recombination, and the resulting strain is selected. Such gene replacement using homologous recombination can be conducted by the method employing a linear DNA, which is known as "Red-driven integration" (Proc. Natl. Acad. Sci. USA, 2000, 97 (12): 6640-6645, WO2005/010175), or by the method employing a plasmid containing a temperature-sensitive replication control region (Proc. Natl. Acad. Sci. USA, 2000, 97 (12): 6640-6645, U.S. Pat. Nos. 6,303,383 and 5,616,480). Furthermore, introduction of a site-specific mutation by gene replacement using homologous recombination as set forth above can also be performed by using a plasmid which is unable to replicate in the host.

Expression of the gene can also be attenuated by insertion of a transposon or an IS factor into the coding region of the gene (U.S. Pat. No. 5,175,107), or by conventional methods, such as mutagenesis treatment with UV irradiation or nitrosoguanidine (N-methyl-N'-nitro-N-nitrosoguanidine).

Inactivation of the gene can also be performed with respect the operon encoding the toxin-antitoxin system.

Production of the YoeB protein, but not the YefM protein, inhibits bacterial cell growth. So, the presence of activity of the YoeB toxin protein can be measured by the method described by, for example, Grady, R. and Hayes, F., (Mol. Microbiol., 47(5); 1419-32 (2003)). Production of the YafQ protein, but not the DinJ protein, also inhibits growth, and the presence of activity of the variant YafQ toxin protein can be measured, for example, in dinJ⁻ yafQ⁻ strains by detecting growth delay due to the variant YafQ toxin protein expression and further complementation of the effect by expression of DinJ antitoxin protein. Production of the MazF protein, but not the MazE protein, also inhibits growth, and the presence of activity of the variant MazF toxin protein can be measured by the method described, for example, by Aizenman, E. et al (Proc. Natl. Acad. Sci. USA, 93 (12); 6059-63 (1996)). Production of the RelE protein, but not the RelB protein, inhibits growth. On the other hand, expression of the RelB protein prevents the lethal or inhibitory effect of the RelE protein. So, the presence of activity of the RelE toxin protein can be demonstrated by the method described by, for example, Gotfredsen, M. and Gerdes, K. (Mol. Microbiol. 29(4), 1065-76 (1998)). Therefore, the reduced or absent activity of the toxin protein in the bacterium according the present invention can be determined when compared to the parent unmodified bacterium. Production of the YeeV protein, but not the YeeU protein, inhibits growth. So, the presence of activity of the YeeV toxin protein can be measured by the method described by, for example, Brown, J. M. and Shaw, K. J. (J. Bacteriol., 185, 22, 6600-6608 (2003)). Therefore, the reduced or absent activity of the YeeV toxin protein in the bacterium according the present invention can be determined when compared to the parent unmodified bacterium. The presence of the HipA protein activity can be detected by complementation of mutation hipA⁻ by the method described, for example, in Moyed, H. S. and Broderick S. H. (J. Bacteriol., 1986, 166(2):399-403). Thus, the reduced or absent activity of the HipA protein in the bacterium according to the present invention can be determined when compared to the parent unmodified bacterium.

The level of gene expression can be estimated by measuring the amount of MRNA transcribed from the gene using various known methods including Northern blotting, quantitative RT-PCR, and the like. The amount or molecular weight of the protein encoded by the gene can be measured by known methods including SDS-PAGE followed by immunoblotting assay (Western blotting analysis) and the like.

Methods for preparation of plasmid DNA, digestion and ligation of DNA, transformation, selection of an oligonucleotide as a primer and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Amino Acid Producing Bacteria

As a bacterium of the present invention which is modified to attenuate expression of a gene encoding a toxin of bacterial toxin-antitoxin pairs, bacteria which are able to produce either aromatic or non-aromatic L-amino acids may be used.

The bacterium of the present invention can be obtained by attenuating expression of a gene encoding a toxin of a bacterial toxin-antitoxin pair in a bacterium which inherently has the ability to produce an L-amino acid. Alternatively, the bacterium of present invention can be obtained by imparting the ability to produce an L-amino acid to a bacterium already having attenuated expression of the gene.

L-Threonine-Producing Bacteria

Examples of parent strains for deriving the L-threonine-producing bacteria of the present invention include, but are not limited to, strains belonging to the genus Escherichia, such as E. coli TDH-6/pVIC40 (VKPM B-3996) (U.S. Pat. No. 5,175,107, U.S. Pat. No. 5,705,371), E. coli 472T23/pYN7 (ATCC 98081) (U.S. Pat. No. 5,631,157), E. coli NRRL-21593 (U.S. Pat. No. 5,939,307), E. coli FERM BP-3756 (U.S. Pat. No. 5,474,918), E. coli FERM BP-3519 and FERM BP-3520 (U.S. Pat. No. 5,376,538), E. coli MG442 (Gusyatiner et al., Genetika (in Russian), 14, 947-956 (1978)), E. coli VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited on Nov. 19, 1987 in the All-Union Scientific Center of Antibiotics (Nagatinskaya Street 3-A, 117105 Moscow, Russian Federation) under the accession number RIA 1867. The strain was also deposited in the Russian National Collection of Industrial Microorganisms (VKPM) (Russia, 117545 Moscow 1, Dorozhny proezd. 1) on Apr. 7, 1987 under the accession number B-3996.

E. coli VKPM B-5318 (EP 0593792B) may also be used as a parent strain for deriving L-threonine-producing bacteria of the present invention. The strain B-5318 is prototrophic with regard to isoleucine, and a temperature-sensitive lambda-phage C1 repressor and PR promoter replaces the regulatory region of the threonine operon in plasmid pVIC40. The strain VKPM B-5318 was deposited in the Russian National Collection of Industrial Microorganisms (VKPM) on May 3, 1990 under accession number of VKPM B-5318.

Preferably, the bacterium of the present invention is additionally modified to enhance expression of one or more of the following genes:

the mutant thrA gene which codes for aspartokinase homoserine dehydrogenase I resistant to feed back inhibition by threonine;

the thrB gene which codes for homoserine kinase;

the thrC gene which codes for threonine synthase;

the rhtA gene which codes for a putative transmembrane protein;

the asd gene which codes for aspartate-β-semialdehyde dehydrogenase; and the aspC gene which codes for aspartate aminotransferase (aspartate transaminase);

The thrA gene which encodes aspartokinase homoserine dehydrogenase I of Escherichia coli has been elucidated (nucleotide positions 337 to 2799, GenBank accession NC_000913.2, gi: 49175990). The thrA gene is located between the thrL and thrB genes on the chromosome of E. coli K-12. The thrB gene which encodes homoserine kinase of Escherichia coli has been elucidated (nucleotide positions 2801 to 3733, GenBank accession NC_000913.2, gi: 49175990). The thrB gene is located between the thrA and thrC genes on the chromosome of E. coli K-12. The thrC gene which encodes threonine synthase of Escherichia coli has been elucidated (nucleotide positions 3734 to 5020, GenBank accession NC_000913.2, gi: 49175990). The thrC gene is located between the thrB gene and the yaaX open reading frame on the chromosome of E. coli K-12. All three genes functions as a single threonine operon. To enhance expression of the threonine operon, the attenuator region which affects the transcription is desirably removed from the operon (WO2005/049808, WO2003/097839).

A mutant thrA gene which codes for aspartokinase homoserine dehydrogenase I resistant to feed back inhibition by threonine, as well as, the thrB and thrC genes can be obtained as one operon from well-known plasmid pVIC40 which is present in the threonine producing *E. coli* strain VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181) and is located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., *Trends Genet.*, 5, 185 (1989)) utilizing primers prepared based on the nucleotide sequence of the gene. The asd genes of other microorganisms can be obtained in a similar manner.

Also, the aspC gene of *E. coli* has already been elucidated (nucleotide positions 983742 to 984932, GenBank accession NC_000913.1, gi:16128895), and can be obtained by PCR. The aspC genes of other microorganisms can be obtained in a similar manner.

L-Lysine-Producing Bacteria

Examples of L-lysine-producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine is present in the culture medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains for deriving L-lysine-producing bacteria of the present invention also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenease (asd), and aspartase (aspA) (EP 1253195 A). In addition, the parent strains may have an increased level of expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations thereof.

Examples of parent strains for deriving L-lysine-producing bacteria of the present invention also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase, lysine decarboxylase (U.S. Pat. No. 5,827, 698), and the malic enzyme (WO2005/010175).

L-Cysteine-Producing Bacteria

Examples of parent strains for deriving L-cysteine-producing bacteria of the present invention include, but are not limited to, strains belonging to the genus *Escherichia*, such as *E. coli* JM15 which is transformed with different cysE alleles coding for feedback-resistant serine acetyltransferases (U.S. Pat. No. 6,218,168, Russian patent application 2003121601); *E. coli* W3110 having over-expressed genes which encode proteins suitable for secreting substances toxic for cells (U.S. Pat. No. 5,972,663); *E. coli* strains having lowered cysteine desulfohydrase activity (JP11155571A2); *E. coli* W3110 with increased activity of a positive transcriptional regulator for cysteine regulon encoded by the cysB gene (WO0127307A1), and the like.

L-Leucine-Producing Bacteria

Examples of parent strains for deriving L-leucine-producing bacteria of the present invention include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); *E. coli* strains obtained by the gene engineering method described in WO96/06926; *E. coli* H-9068 (JP 8-70879 A), and the like.

The bacterium of the present invention may be improved by enhancing the expression of one or more genes involved in L-leucine biosynthesis. Examples include genes of the leuABCD operon, which are preferably represented by a mutant leuA gene coding for isopropylmalate synthase not subject to feedback inhibition by L-leucine (U.S. Pat. No. 6,403,342). In addition, the bacterium of the present invention may be improved by enhancing the expression of one or more genes coding for proteins which excrete L-amino acids from bacterial cells. Examples of such genes include the b2682 and b2683 genes (ygaZH genes) (EP 1239041 A2).

L-Histidine-Producing Bacteria

Examples of parent strains for deriving L-histidine-producing bacteria of the present invention include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No.

6,344,347); *E. coli* H-9341 (FERM BP-6674) (EP1085087); *E. coli* A180/pFM201 (U.S. Pat. No. 6,258,554) and the like.

Examples of parent strains for deriving L-histidine-producing bacteria of the present invention also include strains in which expression of one or more genes encoding an L-histidine biosynthetic enzyme are enhanced. Examples of the L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

It is known that the genes encoding the L-histidine biosynthetic enzyme (hisG, hisBHAFI) are inhibited by L-histidine, and therefore an L-histidine-producing ability can also be efficiently enhanced by introducing a mutation conferring resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been introduced with a vector carrying a DNA encoding an L-histidine-biosynthetic enzyme (JP 56-005099 A), *E. coli* strains introduced with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536), and so forth.

L-Glutamic Acid-Producing Bacteria

Examples of parent strains for deriving L-glutamic acid-producing bacteria of the present invention include, but are not limited to, strains belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in thrC and ilvA genes (U.S. Pat. No. 4,278,765). A wild-type allele of the thrC gene was transferred by the method of general transduction using a bacteriophage P1 grown on the wild-type *E. coli* strain K12 (VKPM B-7) cells. As a result, an L-isoleucine auxotrophic strain VL334thrC$^+$ (VKPM B-8961) was obtained. This strain is able to produce L-glutamic acid.

Examples of parent strains for deriving the L-glutamic acid-producing bacteria of the present invention include, but are not limited to, strains in which expression of one or more genes encoding an L-glutamic acid biosynthetic enzyme are enhanced. Examples of the enzymes involved in L-glutamic acid biosynthesis include glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phophate dehydrogenase, triose phosphate isomerase, fructose bisphosphate aldolase, phosphofructokinase, and glucose phosphate isomerase.

Examples of strains modified so that expression of the citrate synthetase gene, the phosphoenolpyruvate carboxylase gene, and/or the glutamate dehydrogenase gene is/are enhanced include those disclosed in EP1078989A, EP955368A, and EP952221A.

Examples of parent strains for deriving the L-glutamic acid-producing bacteria of the present invention also include strains having decreased or eliminated activity of an enzyme that catalyzes synthesis of a compound other than L-glutamic acid, and branching off from an L-glutamic acid biosynthesis pathway. Examples of such enzymes include isocitrate lyase, α-ketoglutarate dehydrogenase, phosphotransacetylase, acetate kinase, acetohydroxy acid synthase, acetolactate synthase, formate acetyltransferase, lactate dehydrogenase, and glutamate decarboxylase. Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

E. coli W3110sucA::Kmr
E. coli AJ12624 (FERM BP-3853)
E. coli AJ12628 (FERM BP-3854)
E. coli AJ12949 (FERM BP-4881)

*E. coli* W3119sucA::Kmr is a strain obtained by disrupting the α-ketoglutarate dehydrogenase gene (hereinafter referred to as "sucA gene") of *E. coli* W3110. This strain is completely deficient in the α-ketoglutarate dehydrogenase.

Other examples of L-glutamic acid-producing bacterium include those which belong to the genus *Escherichia* and have resistance to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FFRM P-12379, which additionally has a low L-glutamic acid decomposing ability (U.S. Pat. No. 5,393,671); AJ13138 (FERM BP-5565) (U.S. Pat. No. 6,110,714), and the like.

Examples of L-glutamic acid-producing bacteria, include mutant strains belonging to the genus *Pantoea* which are deficient in the α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under an accession number of FERM P-16645. It was then converted to an international deposit under the provisions of the Budapest Treaty on Jan. 11, 1999 and received an accession number of FERM BP-6615. *Pantoea ananatis* AJ13356 is deficient in α-ketoglutarate dehydrogenase activity as a result of disruption of the αKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

L-Phenylalanine-Producing Bacteria

Examples of parent strains for deriving L-phenylalanine-producing bacteria of the present invention include, but are not limited to, strains belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146 and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488424 B1). Furthermore, L-phenylalanine producing bacteria belonging to the genus *Escherichia* with an enhanced activity of the protein encoded by the yedA gene or the yddG gene may also be used (U.S. patent application Ser. Nos. 2003/0148473 A1 and 2003/0157667 A1).

L-Tryptophan-Producing Bacteria

Examples of parent strains for deriving the L-tryptophan-producing bacteria of the present invention include, but are not limited to, strains belonging to the genus *Escherichia*, such as *E. coli* JP4735/pMU3028 (DSM10122) and JP6015/pMU91 (DSM10123) deficient in the tryptophanyl-tRNA synthetase encoded by mutant trpS gene (U.S. Pat. No. 5,756,345); *E. coli* SV164 (pGH5) having a serA allele encoding phosphoglycerate dehydrogenase free from feedback inhibition by serine and a trpE allele encoding anthranilate synthase free from feedback inhibition by tryptophan (U.S. Pat. No. 6,180,373); *E. coli* AGX17 (pGX44) (NRRL B-12263) and AGX6(pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like may be used.

Previously, it was identified that the yddG gene encoding a membrane protein, which is not involved in biosynthetic pathway of any L-amino acid, and imparts to a microorganism resistance to L-phenylalanine and several amino acid analogues when the wild-type allele of the gene was amplified on a multi-copy vector in the microorganism. Besides, the yddG gene can enhance production of L-phenylalanine or L-tryptophan when additional copies are introduced into the cells of the respective producing strain (WO03044192). So it is desirable that the L-tryptophan-producing bacterium be further modified to have enhanced expression of the yddG open reading frame.

Examples of parent strains for deriving the L-tryptophan-producing bacteria of the present invention also include strains in which one or more activities of the enzymes selected from anthranilate synthase, phosphoglycerate dehydrogenase, and tryptophan synthase are enhanced. The anthranilate synthase and phosphoglycerate dehydrogenase are both subject to feedback inhibition by L-tryptophan and L-serine, so that a mutation desensitizing the feedback inhibition may be introduced into these enzymes. Specific examples of strains having such a mutation include a *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains for deriving the L-tryptophan-producing bacteria of the present invention also include strains into which the tryptophan operon which contains a gene encoding desensitized anthranilate synthase has been introduced (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). The tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

L-Proline-Producing Bacteria

Examples of parent strains for deriving L-proline-producing bacteria of the present invention include, but are not limited to, strains belonging to the genus *Escherichia*, such as *E. coli* 702ilvA (VKPM B-8012) which is deficient in the ilvA gene and is able to produce L-proline (EP 1172433). The bacterium of the present invention may be improved by enhancing the expression of one or more genes involved in L-proline biosynthesis. Examples of such genes for L-proline producing bacteria which are preferred include the proB gene coding for glutamate kinase which is desensitized to feedback inhibition by L-proline (DE Patent 3127361). In addition, the bacterium of the present invention may be improved by enhancing the expression of one or more genes coding for proteins excreting L-amino acids from bacterial cells. Such genes are exemplified by b2682 and b2683 genes (ygaZH genes) (EP1239041 A2).

Examples of bacteria belonging to the genus *Escherichia*, which have an activity to produce L-proline include the following *E. coli* strains: NRRL B-12403 and NRRL B-12404 (GB Patent 2075056), VKPM B-8012 (Russian patent application 2000124295), plasmid mutants described in DE Patent 3127361, plasmid mutants described by Bloom F. R. et al (The 15$^{th}$ Miami winter symposium, 1983, p. 34), and the like.

L-Arginine-Producing Bacteria

Examples of parent strains for deriving L-arginine-producing bacteria of the present invention include, but are not limited to, strains belonging to the genus *Escherichia*, such as *E. coli* strain 237 (VKPM B-7925) (U.S. Patent Application 2002/058315 A1) and its derivative strains harboring mutant N-acetylglutamate synthase (Russian Patent Application No. 2001112869), *E. coli* strain 382 (VKPM B-7926) (EP1170358A1), an arginine-producing strain into which argA gene encoding N-acetylglutamate synthase is introduced therein (EP1170361A1), and the like.

Examples of parent strains for deriving L-arginine producing bacteria of the present invention also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase.

L-Valine-Producing Bacteria

Example of parent strains for deriving L-valine-producing bacteria of the present invention include, but are not limited to, strains which have been modified to overexpress the ilvGMEDA operon (U.S. Pat. No. 5,998,178). It is desirable to remove the region of the ilvGMEDA operon which is required for attenuation so that expression of the operon is not attenuated by L-valine that is produced. Furthermore, the ilvA gene in the operon is desirably disrupted so that threonine deaminase activity is decreased.

Examples of parent strains for deriving L-valine-producing bacteria of the present invention include also include mutants having a mutation of amino-acyl t-RNA synthetase (U.S. Pat. No. 5,658,766). For example, *E. coli* VL1970, which has a mutation in the ileS gene encoding isoleucine tRNA synthetase, can be used. *E. coli* VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking $H^+$-ATPase can also be used as parent strains (WO96/06926).

L-Isoleucine-Producing Bacteria

Examples of parent strains for deriving L-isoleucine producing bacteria of the present invention include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used as parent strains (JP 2-458 A, FR 0356739, and U.S. Pat. No. 5,998,178).

2. Method of the Present Invention

The method of the present invention is a method for producing an L-amino acid comprising cultivating the bacterium of the present invention in a culture medium to produce and excrete the L-amino acid into the medium, and collecting the L-amino acid from the medium.

In the present invention, the cultivation, collection, and purification of an L-amino acid from the medium and the like may be performed in a manner similar to conventional fermentation methods wherein an amino acid is produced using a bacterium.

A medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the used microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, and a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Construction of a Strain with an Inactivated yefM-yoeB, dinJ-yafQ, mazEF, relBE, or yeeUV Operon 1. Deletion of the yefM-yoeB, dinJ-yafQ, mazEF, relBE, or yeeUV operon.

A strain having deletion of the yefM-yoeB, dinJ-yafQ, mazEF, relBE, or yeeUV operon was constructed by the method initially developed by Datsenko, K. A. and Wanner, B. L. (Proc. Natl. Acad. Sci. USA, 2000, 97(12), 6640-6645) called "Red-driven integration". According to this procedure, the following PCR primers were constructed;

yoeBL (SEQ ID NO: 3) and yoeBR (SEQ ID NO: 4), which are homologous to both the regions adjacent to the yoeB gene and the gene conferring antibiotic resistance, respectively, in the template plasmid.

yafQL (SEQ ID NO: 9) and yafQR (SEQ ID NO: 10), which are homologous to both the regions adjacent to the yafQ gene and the gene conferring antibiotic resistance, respectively, in the template plasmid.

mazFL (SEQ ID NO: 15) and mazFR (SEQ ID NO: 16), which are homologous to both the regions adjacent to the mazF gene and the gene conferring antibiotic resistance, respectively, in the template plasmid.

relEL (SEQ ID NO: 21) and relER (SEQ ID NO: 22), which are homologous to both the regions adjacent to the relBE operon and the gene conferring antibiotic resistance, respectively, in the template plasmid.

yeeVL (SEQ ID NO: 27) and yeeVR (SEQ ID NO: 28), which are homologous to both the regions adjacent to the yeeUV operon and the gene conferring antibiotic resistance, respectively, in the template plasmid.

The plasmid pACYC184 (NBL Gene Sciences Ltd., UK) (GenBank/EMBL accession number X06403) was used as a template in the PCR reaction. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

A 1152 bp PCR product (FIG. 1, 3, 5, 7, or 9) was obtained and was purified in agarose gel and used for electroporation of E. coli MG1655 (ATCC 700926), which contains the plasmid pKD46 having a temperature-sensitive replication origin. The plasmid pKD46 (Datsenko, K. A. and Wanner, B. L., Proc. Natl. Acad. Sci. USA, 2000, 97:12:6640-45) includes a 2,154 nucleotide (31088-33241) DNA fragment of phage λ (GenBank accession No. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of E. coli MG1655.

Electrocompetent cells were prepared as follows: E. coli MG1655/pKD46 was grown overnight at 30° C. in LB medium containing 100 mg/l of ampicillin, and the culture was diluted 100 times with 5 ml of SOB medium (Sambrook et al, "Molecular Cloning A Laboratory Manual, Second Edition", Cold Spring Harbor Laboratory Press (1989)) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and ≈100 ng of PCR product. Cells after electroporation were incubated with 1 ml of SOC medium (Sambrook et al, "Molecular Cloning A Laboratory Manual, Second Edition", Cold Spring Harbor Laboratory Press (1989)) at 37° C. for 2.5 hours and then were plated onto L-agar containing chloramphenicol (30 µg/ml) and grown at 37° C. to select $Cm^R$ recombinants. Then, to eliminate the pKD46 plasmid, 2 passages on L-agar with Cm at 42° C. were performed and the obtained colonies were tested for sensitivity to ampicillin.

2. Verification of the Operon Deletion by PCR

The mutants, which have the yefM-yoeB, dinJ-yafQ, mazEF, relBE, or yeeUV operon deleted, marked with the Cm resistance gene, were verified by PCR. Locus-specific primers yoeB1 (SEQ ID NO: 5) and yoeB2 (SEQ ID NO: 6), yafQ1 (SEQ ID NO: 11) and yafQ2 (SEQ ID NO: 12), mazF1 (SEQ ID NO: 17) and mazF2 (SEQ ID NO: 18), relE1 (SEQ ID NO: 23) and relE2 (SEQ ID NO: 24), yeeV1 (SEQ ID NO: 29) and yeeV2 (SEQ ID NO: 30) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR products obtained in the reaction with the cells of the parental strain MG1655 as the template was 835 bp for the primers yoeB1 and yoeB2, 645 bp for the primers yafQ1 and yafQ2, 688 bp for the primers mazF1 and mazF2, 579 bp for the primers relE1 and relE2, and 975 bp for the primers yeeV1 and yeeV2, in length, respectively. The PCR products obtained in the reaction with the cells of MG1655 ΔyefM-yoeB::cat, MG1655 ΔdinJ-yafQ::cat, MG1655 ΔmazEF::cat, and MG1655 ΔrelBE::cat as the template were 1303, 1255, 1256, 1204, and 1223 bp in length, respectively (FIGS. 2, 4, 6, 8, and 10).

Example 2

Construction of a Strain with the Inactivated hipA Gene

1. Preparation of the PCR template and helper plasmids

The PCR template plasmid pMW118-attL-Cm-attR and the helper plasmid pMW-intxis-ts were prepared as follows:

(1) pMW118-attL-Cm-attR

Figure 11:
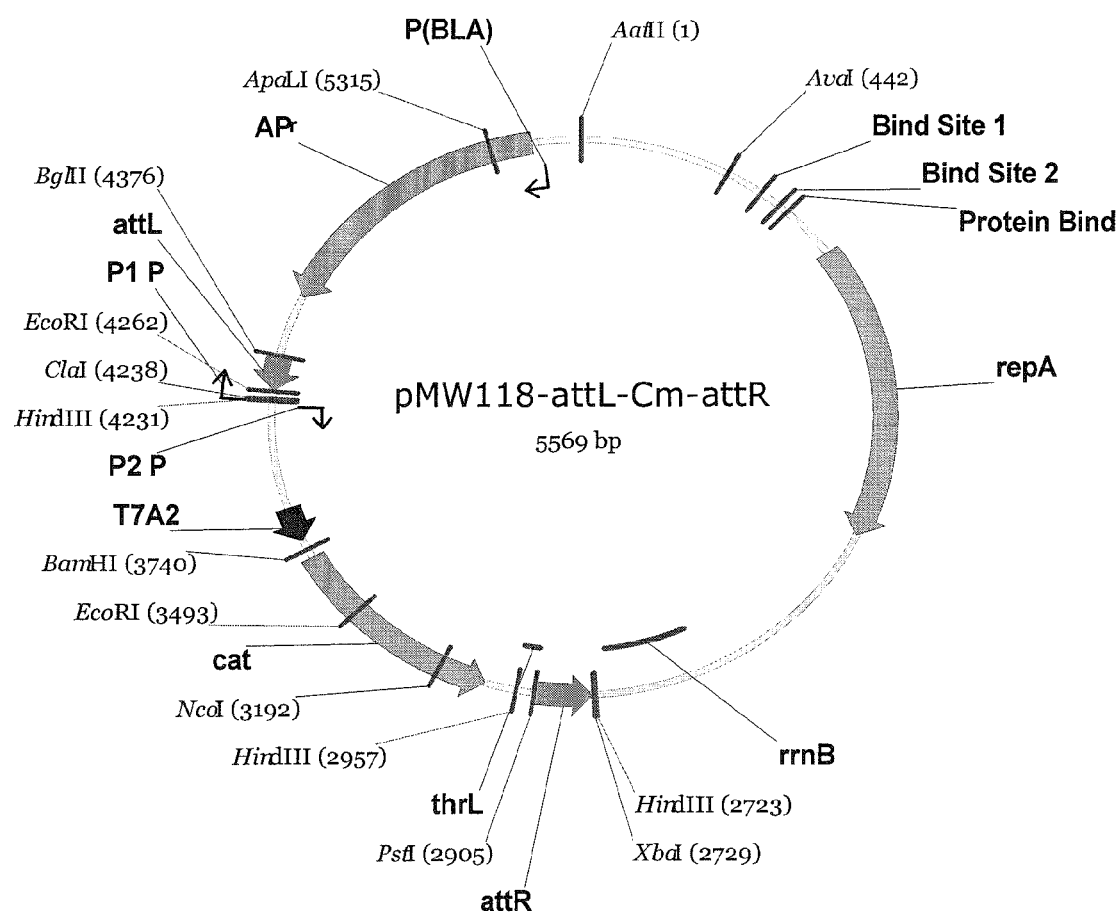
FIG. 11 shows the construction of the pMW118-attL-Cm-attR plasmid used as the template for PCR.

The pMW118-attL-Cm-attR plasmid was constructed on the basis of pMW118-attL-Tc-attR that was obtained by ligation of the following four DNA fragments:

1) the BglII-EcoRI fragment (114 bp) carrying attL (SEQ ID NO: 33) which was obtained by PCR amplification of the corresponding region of the E. coli W3350 (contained λ prophage) chromosome using oligonucleotides P1 and P2 (SEQ ID NOS: 34 and 35) as primers (these primers contained the subsidiary recognition sites for BglII and EcoRI endonucleases);

2) the PstI-HindIII fragment (182 bp) carrying attR (SEQ ID NO: 36) which was obtained by PCR amplification of the corresponding region of the E. coli W3350 (contained λ prophage) chromosome using the oligonucleotides P3 and P4 (SEQ ID NOS: 37 and 38) as primers (these primers contained the subsidiary recognition sites for PstI and HindIII endonucleases);

3) the large BglII-HindIII fragment (3916 bp) of pMW118-ter_rrnB. The plasmid pMW118-ter_rrnB was obtained by ligation of the following three DNA fragments:

the large DNA fragment (2359 bp) carrying the AatII-EcoRI fragment of pMW118 that was obtained by the following way: pMW118 was digested with EcoRI restriction endonuclease, treated with Klenow fragment of DNA polymerase I, and then digested with AatII restriction endonuclease;

the small AatII-BglII fragment (1194 bp) of pUC19 carrying the bla gene for ampicillin resistance ($Ap^R$) was obtained by PCR amplification of the corresponding region of the pUC19 plasmid using oligonucleotides P5 and P6 (SEQ ID NOS: 39 and 40) as primers (these primers contained the subsidiary recognition sites for AatII and BglII endonucleases);

the small BglII-PstIpol fragment (363 bp) of the transcription terminator ter_rrnB was obtained by PCR amplification of the corresponding region of the E. coli MG1655 chromosome using oligonucleotides P7 and P8 (SEQ ID NOS: 41 and 42) as primers (these primers contained the subsidiary recognition sites for BglII and PstI endonucleases);

4) the small EcoRI-PstI fragment (1388 bp) (SEQ ID NO: 43) of pML-Tc-ter_thrL bearing the tetracycline resistance gene and the ter_thrL transcription terminator; the pML-Tc-ter_thrL plasmid was obtained in two steps:

the pML-ter_thrL plasmid was obtained by digesting the pML-MCS plasmid (Mashko, S. V. et al., Biotekhnologiya (in Russian), 2001, no. 5, 3-20) with the XbaI and BamHI restriction endonucleases, followed by ligation of the large fragment (3342 bp) with the XbaI-BamHI fragment (68 bp) carrying terminator ter_thrL obtained by PCR amplification of the corresponding region of the E. coli MG1655 chromosome using oligonucleotides P9 and P10 (SEQ ID NOS: 44 and 45) as primers (these primers contained the subsidiary recognition sites for the XbaI and BamHI endonucleases);

the pML-Tc-ter_thrL plasmid was obtained by digesting the pML-ter_thrL plasmid with the KpnI and XbaI restriction endonucleases followed by treatment with Klenow fragment of DNA polymerase I and ligation with the small EcoRI-Van9II fragment (1317 bp) of pBR322 bearing the tetracycline resistance gene (pBR322 was digested with EcoRI and Van9II restriction endonucleases and then treated with Klenow fragment of DNA polymerase I);

The pMW118-attL-Cm-attR plasmid (FIG. 11) was constructed by ligation of the large BamHI-XbaI fragment (4413 bp) of pMW118-attL-Tc-attR and the artificial DNA BglII-XbaI fragment (1162 bp) containing the $P_{A2}$ promoter (the early promoter of the phage T7), the cat gene for chloramphenicol resistance ($Cm^R$), the ter_thrL transcription terminator, and attR. The artificial DNA fragment (SEQ ID NO: 46) was obtained as follows:

1. The pML-MCS plasmid was digested with the KpnI and XbaI restriction endonucleases and ligated with the small KpnI-XbaI fragment (120 bp), which included the $P_{A2}$ promoter (the early promoter of phage T7) obtained by PCR amplification of the corresponding DNA region of phage T7 using oligonucleotides P11 and P12 (SEQ ID NOS: 47 and 48, respectively) as primers (these primers contained the subsidiary recognition sites for KpnI and XbaI endonucleases). As a result, the pML-$P_{A2}$-MCS plasmid was obtained.

2. The XbaI site was deleted from pML-$P_{A2}$-MCS. As a result, the pML-$P_{A2}$-MCS(XbaI$^-$) plasmid was obtained.

3. The small BglII-HindIII fragment (928 bp) of pML-$P_{A2}$-MCS(XbaI$^-$) containing the $P_{A2}$ promoter (the early promoter of the phage T7) and the cat gene for chloramphenicol resistance ($Cm^R$) was ligated with the small HindIII-HindIII fragment (234 bp) of pMW118-attL-Tc-attR containing the ter_thrL transcription terminator and attR.

4. The required artificial DNA fragment (1156 bp) was obtained by PCR amplification of the ligation reaction mixture using oligonucleotides P9 and P4 (SEQ ID NOS: 44 and 38) as primers (these primers contained the subsidiary recognition sites for HindIII and XbaI endonucleases).

(2) pMW-intxis-ts

Recombinant plasmid pMW-intxis-ts containing the cI repressor gene and the int-xis genes of phage λ under control of promoter $P_R$ was constructed on the basis of vector pMW-$P_{lac}$lacI-ts. To construct the pMWP$_{lac}$lacI-ts variant, the AatII-EcoRV fragment of the pMWP$_{lac}$lacI plasmid (Skorokhodova, A. Yu. et al., Biotekhnologiya (in Russian), 2004, no. 5, 3-21) was substituted with the AatII-EcoRV fragment of the pMAN997 plasmid (Tanaka, K. et al., J. Bacteriol., 2001, 183(22): 6538-6542) bearing the par and ori loci and the repA$^{ts}$ gene of the pSC101 replicon.

Two DNA fragments were amplified using phage λ DNA ("Fermentas") as a template. The first one contained the DNA sequence from 37168 to 38046, the cI repressor gene, promoters $P_{RM}$ and $P_R$, and the leader sequence of the cro gene. This fragment was PCR-amplified using oligonucleotides P13 and P14 (SEQ ID NOS: 49 and 50) as primers. The second DNA fragment containing the xis-int genes of phage λ and the DNA sequence from 27801 to 29100 was PCR-amplified using oligonucleotides P15 and P16 (SEQ ID NOS: 51 and 52) as primers. All primers contained the corresponding restriction sites.

The first PCR-amplified fragment carrying the cI repressor was digested with restriction endonuclease ClaI, treated with Klenow fragment of DNA polymerase I, and then digested with restriction endonuclease EcoRI. The second PCR-amplified fragment was digested with restriction endonucleases EcoRI and PstI. The pMWP$_{lac}$lacI-ts plasmid was digested with the BglII endonuclease, treated with Klenow fragment of DNA polymerase I, and digested with the PstI restriction endonuclease. The vector fragment of pMWPlaclacI-ts was eluted from the agarose gel and ligated with the above-mentioned digested PCR-amplified fragments to obtain the pMW-intxis-ts recombinant plasmid.

2. Construction of a strain with the inactivated hipA gene (1) Deletion of the hipA gene A strain having deletion of the hipA gene was constructed by the method initially developed by Datsenko, K. A. and Wanner, B. L. (Proc. Natl. Acad. Sci. USA, 2000, 97(12): 6640-6645) called "Red-driven integration". The DNA fragment containing the Cm$^R$ marker encoded by the cat gene was obtained by PCR, using primers P17 (SEQ ID NO: 53) and P18 (SEQ ID NO: 54) and plasmid pMW118-attL-Cm-attR as the template. Primer P17 contains both a region complementary to the 36-nt region located at the 5' end of the hipA gene and a region complementary to the attL region. Primer P18 contains both a region complementary to the 35-nt region located at the 3' end of the hipA gene and a region complementary to the attR region. Conditions for PCR were as follows: denaturation step: 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

Figure 12:
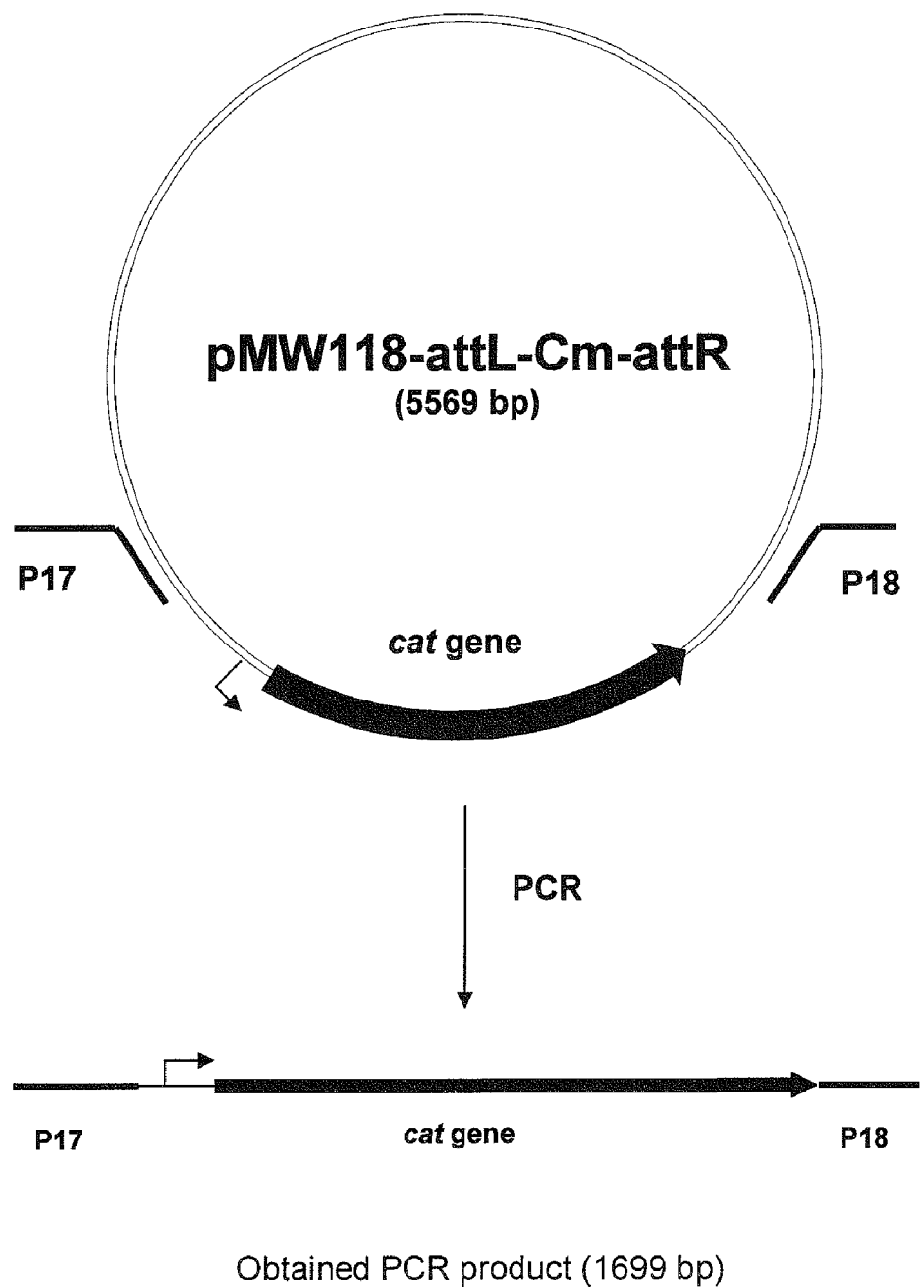
FIG. 12 shows the relative positions of primers P17 and P18 on plasmid pMW118-attL-Cm-attR used for PCR amplification of the cat gene.

A 1699-bp PCR product (FIG. 12) was obtained and purified in agarose gel and was used for electroporation of E. coli MG1655 (ATCC 700926), which contains the pKD46 plasmid having temperature-sensitive replication. According to the method as described in Example 1, electrocompetent cells were prepared and electroporation was performed, and mutants with deletion of the hipA gene were obtained.

(2) Verification of the hipA gene deletion by PCR

Figure 13:
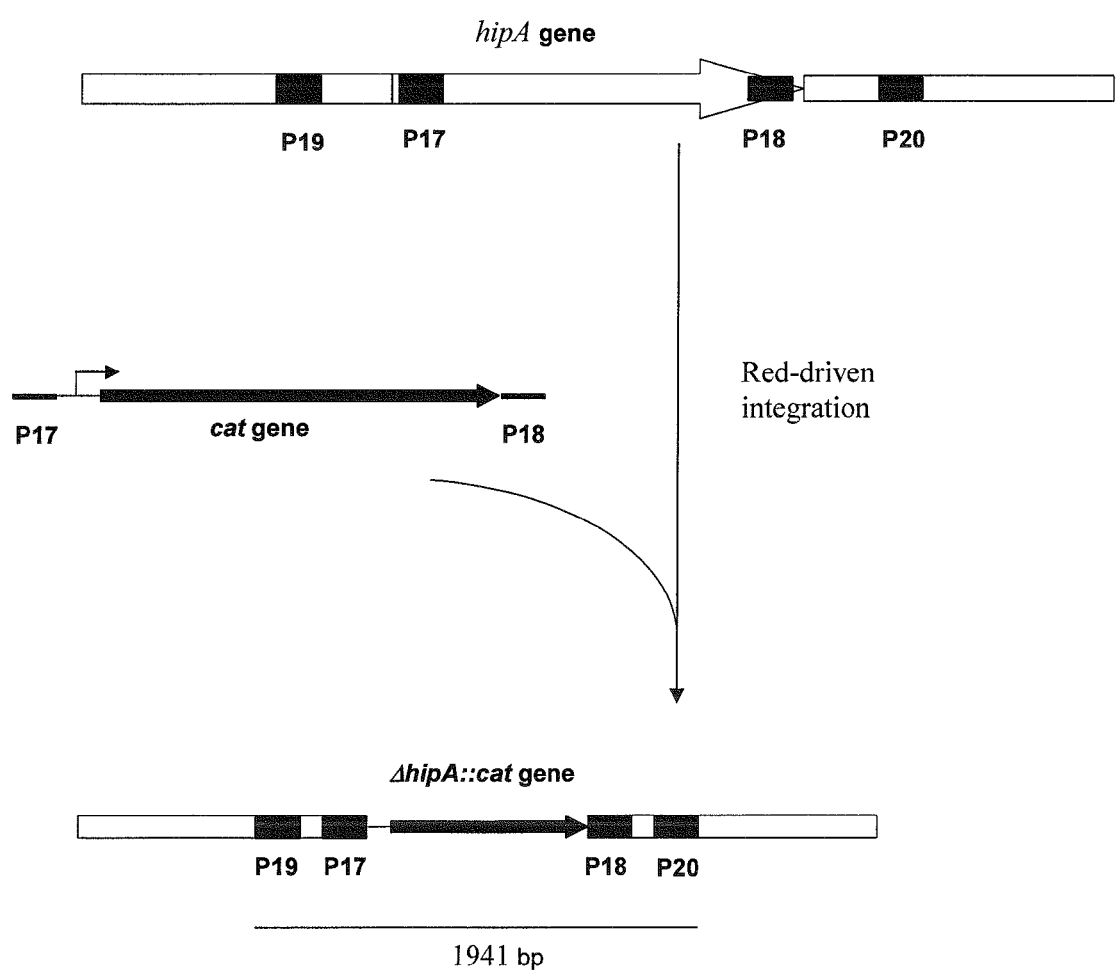
FIG. 13 shows the construction of the chromosomal DNA fragment comprising the inactivated hipA gene.

The mutants having the hipA gene deleted and marked with the Cm resistance gene were verified by PCR. Locus-specific primers P19 (SEQ ID NO: 55) and P20 (SEQ ID NO: 56) were used in PCR for verification. Conditions for PCR verification were as follows: denaturation step: 3 min at 94° C.; profile for the 30 cycles: 30 sec at 94° C., 30 sec at 54° C., 1 min at 72° C.; final step: 7 min at 72° C. The PCR product obtained in the reaction with the cells of the parental hipA$^+$ MG1655 strain as the template was 1564 bp in length. The PCR product obtained in the reaction with the cells of the mutant strain as the template was 1941 bp in length (FIG. 13). The mutant strain was named MG1655 ΔhipA::cat.

Example 3

Production of L-threonine by E. coli B-3996-ΔyefM-yoeB, B-3996-ΔdinJ-yafQ, B-3996-ΔmazEF, or B-3996-ΔhipA To test the effect of inactivation of the yefM-yoeB, dinJ-yafQ, or mazEF operon on threonine production, DNA fragments from the chromosome of the above-described E. coli MG1655 ΔyefM-yoeB::cat, MG1655 ΔdinJ-yafQ::cat, or MG1655 ΔmazEF::cat were transferred to the threonine-producing E. coli VKPM B-3996 by P1 transduction (Miller, J. H. (1972) Experiments in Molecular Genetics, Cold Spring Harbor Lab. Press, Plainview, N.Y.) to obtain the strain B-3996-ΔyefM-yoeB, B-3996-ΔdinJ-yafQ, or B-3996-ΔmazEF.

E. coli B-3996, B-3996-ΔyefM-yoeB, B-3996-ΔdinJ-yafQ, and B-3996-ΔmazEF were grown for 18-24 hours at 37° C. on L-agar plates. To obtain a seed culture, the strains were grown on a rotary shaker (250 rpm) at 32° C. for 18 hours in 20×200 mm test tubes containing 2 ml of L-broth with 4% sucrose. Then, the fermentation medium was inoculated with 0.21 ml (10%) seed material. The fermentation was performed in 2 ml of minimal medium for fermentation in 20×200 mm test tubes. Cells were grown for 65 hours at 32° C. with shaking at 250 rpm.

After cultivation, the amount of L-threonine which had accumulated in the medium was determined by paper chromatography using the following mobile phase:butanol:acetic acid:water=4::1 (v/v). A solution (2%) of ninhydrin in acetone was used as a visualizing reagent. A spot containing L-threonine was cut out, L-threonine was eluted in 0.5% water solution of $CdCl_2$, and the amount of L-threonine was estimated spectrophotometrically at 540 nm. The results of 10 independent test tube fermentations are shown in Table 1.

DNA fragments from the chromosome of the above-described E. coli MG1655 ΔhipA::cat were transferred to E. coli B-3996 in the same way as described above, and the strain B-3996-ΔhipA was obtained. E. coli B-3996 and B-3996-ΔhipA were cultivated for L-threonine production in the same way. The results of 10 independent test tube fermentations are shown in Table 2.

The composition of the fermentation medium (g/l) was as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 |

Glucose and magnesium sulfate were sterilized separately. $CaCO_3$ was sterilized by dry-heat at 180° C. for 2 hours. The pH was adjusted to 7.0. Antibiotic was introduced into the medium after sterilization.

TABLE 1

| Strain | OD$_{540}$ | Amount of L-threonine, g/l |
|---|---|---|
| B-3996 | 26.1 ± 0.5 | 23.4 ± 0.3 |
| B-3996-ΔyefM-yoeB | 22.7 ± 0.6 | 24.4 ± 0.8 |
| B-3996-ΔdinJ-yafQ | 22.5 ± 0.9 | 24.9 ± 1.2 |
| B-3996-ΔmazEF | 26.5 ± 1.1 | 24.1 ± 0.6 |

TABLE 2

| Strain | OD$_{540}$ | Amount of L-threonine, g/l |
|---|---|---|
| B-3996 | 32.1 ± 0.6 | 21.3 ± 0.2 |
| B-3996-ΔhipA | 31.6 ± 0.3 | 22.4 ± 0.4 |

It can be seen from Tables 1 and 2 that B-3996-ΔyefM-yoeB, B-3996-ΔdinJ-yafQ, B-3996-ΔmazEF, and B-3996-ΔhipA caused accumulation of a higher amount of L-threonine as compared with B-3996.

DNA fragments from the chromosome of the above-described *E. coli* MG1655 ΔrelBE::cat or *E. coli* MG1655 ΔyeeUV::cat can be transferred to the threonine-producing *E. coli* strain VKPM B-3996 to inactivate the relBE or yeeUV operon of the strain VKPM B-3996 in the same manner as described above.

Example 4

Production of L-lysine by *E. coli* WC196 (pCABD2)-ΔyefM-yoeB, WC196(pCABD2)-ΔdinJ-yafQ, WC196(pCABD2)-ΔmazEF, WC196 (pCABD2)-ΔrelBE, WC196(pCABD2)-ΔyeeUV, or WC196(pCABD2)-ΔhipA To test the effect of inactivation of the yefM-yoeB, dinJ-yafQ, mazEF, relBE, yeeUV, or hipA operon on lysine production, DNA fragments from the chromosome of the above-described *E. coli* MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the lysine-producing *E. coli* strain WC196 (pCABD2) by P1 transduction (Miller, J. H. (1972) Experiments in Molecular Genetics, Cold Spring Harbor Lab. Press, Plainview, N.Y.) to obtain the strain WW196(pCABD2)-ΔyefM-yoeB, WW196(pCABD2)-ΔdinJ-yafQ, WW196 (pCABD2)-ΔmazEF, WW196(pCABD2)-ΔrelBE, WW196 (pCABD2)-ΔyeeUV, or WW196(pCABD2)-ΔhipA. pCABD2 is a plasmid which includes a dapA gene coding for a dihydrodipicolinate synthase having a mutation which desensitizes feedback inhibition by L-lysine, a lysC gene coding for aspartokinase III having a mutation which desensitizes feedback inhibition by L-lysine, a dapB gene coding for a dihydrodipicolinate reductase gene, a ddh gene coding for diaminopimelate dehydrogenase, and a streptomycin resistance gene (U.S. Pat. No. 6,040,160).

*E. coli* WW196(pCABD2), WW196(pCABD2)-ΔyefM-yoeB, WW196(pCABD2)-ΔdinJ-yafQ, WW196(pCABD2)-ΔmazEF, WW196(pCABD2)-ΔrelBE, WW196(pCABD2)-ΔyeeUV, or WW196(pCABD2)-ΔhipA can be cultured in the L-medium containing 20 mg/l of streptomycin at 37° C. 0.3 ml of the obtained cultures can each be inoculated into 20 ml of the fermentation medium containing the required drugs in a 500 ml-flask. The cultivation can be carried out at 37° C. for 16 hours by using a reciprocal shaker at the agitation speed of 115 rpm. After the cultivation, the amounts of L-lysine and residual glucose in the medium can be measured by a known method (Biotech-analyzer AS210, manufactured by Sakura Seiki Co.). Then, the yield of L-lysine relative to consumed glucose can be calculated for each of the strains.

The composition of the fermentation medium (g/l) is as follows:

| | |
|---|---|
| Glucose | 40 |
| $(NH_4)_2SO_4$ | 24 |
| $K_2HPO_4$ | 1.0 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Yeast extract | 2.0 | pH is adjusted to 7.0 by KOH and the medium is autoclaved at 115° C. for 10 min. Glucose and $MgSO_4.7H_2O$ are sterilized separately. 30 g/l of $CaCO_3$, which has been dry-heat sterilized at 180° C. for 2 hours, is added.

Example 5

Production of L-cysteine by *E. coli* JM15(ydeD)-ΔyefM-yoeB, JM15(ydeD)-ΔdinJ-yafQ, JM15 (ydeD)-ΔmazEF, JM15(ydeD)-ΔrelBE, JM15 (ydeD)-ΔyeeUV, or JM15(ydeD)-ΔhipA To test the effect of inactivation of the yefM-yoeB, dinJ-yafQ, mazEF, relBE, yeeUV, or hipA operon on L-cysteine production, DNA fragments from the chromosome of the above-described *E. coli* MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the *E. coli* L-cysteine producing strain JM15(ydeD) by P1 transduction (Miller, J. H. (1972) Experiments in Molecular Genetics, Cold Spring Harbor Lab. Press, Plainview, N.Y.) to obtain the strain JM15(ydeD)-ΔyefM-yoeB, JM15(ydeD)-ΔdinJ-yafQ, JM15(ydeD)-ΔmazEF, JM15(ydeD)-ΔrelBE, JM15(ydeD)-ΔyeeUV, or JM15 (ydeD)-ΔhipA. The strain JM15 (CGSC# 5042) can be obtained from The Coli Genetic Stock Collection at the *E. coli* Genetic Resource Center, MCD Biology Department, Yale University.

*E. coli* JM15(ydeD) is a derivative of *E. coli* JM15 (U.S. Pat. No. 6,218,168) which can be transformed with DNA having the ydeD gene, which codes for a membrane protein, and is not involved in a biosynthetic pathway of any L-amino acid (U.S. Pat. No. 5,972,663).

Fermentation conditions for evaluation of L-cysteine production are described in detail in Example 6 of U.S. Pat. No. 6,218,168.

Example 6

Production of L-leucine by *E. coli* 57-ΔyefM-yoeB, 57-ΔdinJ-yafQ, 57-ΔmazEF, 57-ΔrelBE, 57-ΔyeeUV, or 57-ΔhipA To test the effect of inactivation of the yefM-yoeB, dinJ-yafQ, mazEF, relBE, yeeUV, or hipA operon on L-leucine production, DNA fragments from the chromosome of the above-described *E. coli* MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the *E. coli* L-leucine producing strain 57

(VKPM B-7386, U.S. Pat. No. 6,124,121) by P1 transduction (Miller, J. H. (1972) Experiments in Molecular Genetics, Cold Spring Harbor Lab. Press, Plainview, N.Y.) to obtain the strain 57-pMW-ΔyefM-yoeB, 57-ΔdinJ-yafQ, 57-ΔmazEF, 57-ΔrelBE, 57-ΔyeeUV, or 57-ΔhipA. The strain 57 has been deposited in the Russian National Collection of Industrial Microorganisms (VKPM) (Russia, 117545 Moscow, 1 Dorozhny proezd, 1) on May 19, 1997 under accession number VKPM B-7386.

E. coli 57, 57-ΔyefM-yoeB, 57-ΔdinJ-yafQ, 57-ΔmazEF, 57-ΔrelBE, 57-ΔyeeUV, or 57-ΔhipA can be cultured for 18-24 hours at 37° C. on L-agar plates. To obtain a seed culture, the strains can be grown on a rotary shaker (250 rpm) at 32° C. for 18 hours in 20×200 mm test tubes containing 2 ml of L-broth with 4% sucrose. Then, the fermentation medium can be inoculated with 0.21 ml (10%) seed material. The fermentation can be performed in 2 ml of minimal medium for fermentation in 20×200 mm test tubes. Cells can be grown for 48-72 hours at 32° C. with shaking at 250 rpm. The amount of L-leucine can be measured by paper chromatography (liquid phase composition: butanol—acetic acid—water=4:1:1)

The composition of the fermentation medium (g/l) is as follows (pH 7.2):

| | |
|---|---|
| Glucose | 60.0 |
| $(NH_4)_2SO_4$ | 25.0 |
| $K_2HPO_4$ | 2.0 |
| $MgSO_4 \cdot 7H_2O$ | 1.0 |
| Thiamine | 0.01 |
| $CaCO_3$ | 25.0 |

Glucose and $CaCO_3$ are sterilized separately.

Example 7

Production of L-histidine by E. coli 80-ΔyefM-yoeB, 80-ΔdinJ-yafQ, 80-ΔmazEF, 80-ΔrelBE, 80-ΔyeeUV, or 80-ΔhipA To test the effect of inactivation of the yefM-yoeB, dinJ-yafQ, mazEF, relBE, yeeUV, or hipA operon on L-histidine production, DNA fragments from the chromosome of the above-described E. coli MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the histidine-producing E. coli strain 80 by P1 transduction (Miller, J. H. (1972) Experiments in Molecular Genetics, Cold Spring Harbor Lab. Press, Plainview, N.Y.) to obtain the strain 80-ΔyefM-yoeB, 80-ΔdinJ-yafQ, 80-ΔmazEF, 80-ΔrelBE, 80-ΔyeeUV, or 80-ΔhipA. The strain 80 has been deposited in the Russian National Collection of Industrial Microorganisms (Russia, 117545 Moscow, 1 Dorozhny proezd, 1) on Oct. 15, 1999 under accession number VKPM B-7270 and then converted to a deposit under the Budapest Treaty on Jul. 12, 2004.

E. coli 80, 80-ΔyefM-yoeB, 80-ΔdinJ-yafQ, 80-ΔmazEF, 80-ΔrelBE, 80-ΔyeeUV, or 80-ΔhipA can be cultivated in L-broth for 6 hours at 29° C. Then, 0.1 ml of obtained cultures can each be inoculated into 2 ml of fermentation medium in 20×200 mm test tube and cultivated for 65 hours at 29° C. with a rotary shaker (350 rpm). After cultivation, the amount of histidine which accumulates in the medium can be determined by paper chromatography. The paper can be developed with a mobile phase:n-butanol:acetic acid:water=4:1:1 (v/v). A solution of ninhydrin (0.5%) in acetone can be used as a visualizing reagent.

The composition of the fermentation medium (g/l) is as follows (pH 6.0):

| | |
|---|---|
| Glucose | 100.0 |
| Mameno (soybean hydrolysate) | 0.2 as total nitrogen |
| L-proline | 1.0 |
| $(NH_4)_2SO_4$ | 25.0 |
| $KH_2PO_4$ | 2.0 |
| $MgSO_4 \cdot 7H_2O$ | 1.0 |
| $FeSO_4 \cdot 7H_2O$ | 0.01 |
| $MnSO_4$ | 0.01 |
| Thiamine | 0.001 |
| Betaine | 2.0 |
| $CaCO_3$ | 60.0 |

Glucose, proline, betaine and $CaCO_3$ are sterilized separately. pH is adjusted to 6.0 before sterilization.

Example 8

Production of L-glutamate by E. coli VL334thrC$^+$-ΔyefM-yoeB, VL334thrC$^+$-ΔdinJ-yafQ, VL334thrC$^+$-ΔmazEF, VL334thrC$^+$-ΔrelBE, VL334thrC$^+$-ΔyeeUV, or VL334thrC$^+$-ΔhipA To test the effect of inactivation of the yefM-yoeB, dinJ-yafQ, mazEF, relBE, yeeUV, or hipA operon on L-glutamate production, DNA fragments from the chromosome of the above-described E. coli MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the E. coli L-glutamate producing strain VL334thrC$^+$ (EP 1172433) by P1 transduction (Miller, J. H. (1972) Experiments in Molecular Genetics, Cold Spring Harbor Lab. Press, Plainview, N.Y.) to obtain the strain VL334thrC$^+$-ΔyefM-yoeB, VL334thrC$^+$-ΔdinJ-yafQ, VL334thrC$^+$-ΔmazEF, VL334thrC$^+$-ΔrelBE, VL334thrC$^+$-ΔyeeUV, or VL334thrC$^+$-ΔhipA. The strain VL334thrC$^+$ has been deposited in the Russian National Collection of Industrial Microorganisms (VKPM) (Russia, 117545 Moscow, 1 Dorozhny proezd, 1) on Dec. 6, 2004 under the accession number VKPM B-8961 and then converted to a deposit under the Budapest Treaty on Dec. 8, 2004.

E. coli VL334thrC$^+$, VL334thrC$^+$-ΔyefM-yoeB, VL334thrC$^+$-ΔdinJ-yafQ, VL334thrC$^+$-ΔmazEF, VL334thrC$^+$-ΔrelBE, VL334thrC$^+$-ΔyeeUV, or VL334thrC$^+$-ΔhipA can be grown for 18-24 hours at 37° C. on L-agar plates. Then, one loop of the cells can be transferred into test tubes containing 2 ml of fermentation medium. The fermentation medium should contain 60 g/l glucose, 25 g/l ammonium sulfate, 2 g/l $KH_2PO_4$, 1 g/l $MgSO_4$, 0.1 mg/ml thiamine, 70 μg/ml L-isoleucine and 25 g/l $CaCO_3$ (pH 7.2). Glucose and $CaCO_3$ should be sterilized separately. Cultivation can be carried out at 30° C. for 3 days with shaking. After the cultivation, the amount of L-glutamic acid produced can be determined by paper chromatography (liquid phase composition: butanol-acetic acid-water=4:1:1) with subsequent staining by ninhydrin (1% solution in acetone) and further elution of the compounds in 50% ethanol with 0.5% $CdCl_2$.

Example 9

Production of L-phenylalanine by E. coli AJ12739-ΔyefM-yoeB, AJ12739-ΔdinJ-yafQ, AJ12739-ΔmazEF, AJ12739-ΔrelBE, AJ12739-ΔyeeUV, or AJ12739-ΔhipA To test the effect of inactivation of the yefM-yoeB, dinJ-yafQ, mazEF, relBE, yeeUV, or hipA operon on L-phenylalanine production, DNA fragments from the chromosome of the above-described E. coli MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the phenylalanine-producing E. coli strain AJ12739 by P1 transduction (Miller, J. H. (1972) Experiments in Molecular Genetics, Cold Spring Harbor Lab. Press, Plainview, N.Y.) to obtain the strain AJ12739-ΔyefM-yoeB, AJ12739-ΔdinJ-yafQ, AJ12739-ΔmazEF, AJ12739-ΔrelBE, AJ12739-ΔyeeUV, or AJ12739-ΔhipA. The strain AJ12739 has been deposited in the Russian National Collection of Industrial Microorganisms (VKPM) (Russia, 117545 Moscow, 1 Dorozhny proezd, 1) on Nov. 6, 2001 under accession number VKPM B-8197 and then converted to a deposit under the Budapest Treaty on Aug. 23, 2002.

E. coli AJ12739, AJ12739-ΔyefM-yoeB, AJ12739-ΔdinJ-yafQ, AJ12739-ΔmazEF, AJ12739-ΔrelBE, AJ12739-ΔyeeUV, or AJ12739-ΔhipA can be cultivated at 37° C. for 18 hours in a nutrient broth. 0.3 ml of the obtained cultures can each be inoculated into 3 ml of a fermentation medium in a 20×200 mm test tube and cultivated at 37° C. for 48 hours with a rotary shaker. After cultivation, the amount of phenylalanine which accumulates in the medium can be determined by TLC. 10×15 cm TLC plates coated with 0.11 mm layers of Sorbfil silica gel without fluorescent indicator (Stock Company Sorbpolymer, Krasnodar, Russia) can be used. Sorbfil plates can be developed with a mobile phase: propan-2-ol:ethylacetate:25% aqueous ammonia:water=40:40:7:16 (v/v). A solution (2%) of ninhydrin in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is sterilized by dry-heat at 180° C. for 2 hours. pH is adjusted to 7.0.

Example 10

Production of L-tryptophan by E. coli SV164 (pGH5)-ΔyefM-yoeB, SV164(pGH5)-ΔdinJ-yafQ, SV164(pGH5)-ΔmazEF, SV164(pGH5)-ΔrelBE, SV164(pGH5)-ΔyeeUV, or SV164(pGH5)-ΔhipA To test the effect of inactivation of the yefM-yoeB, dinJ-yafQ, mazEF, relBE, or hipA operon on L-tryptophan production, DNA fragments from the chromosome of the above-described E. coli MG1655 ΔyefM-yoeB::cat, MG1655 ΔdinJ-yafQ::cat, MG1655 ΔmazEF::cat, MG1655 ΔrelBE::cat, MG1655ΔyeeUV::cat, or MG1655 ΔhipA::cat can be transferred to tryptophan-producing E. coli strain SV164 (pGH5) by P1 transduction (Miller, J. H. (1972) Experiments in Molecular Genetics, Cold Spring Harbor Lab. Press, Plainview, N.Y.) to obtain the strain SV164(pGH5)-ΔyefM-yoeB, SV164(pGH5)-ΔdinJ-yafQ, SV164(pGH5)-ΔmazEF, SV164(pGH5)-ΔrelBE, SV164(pGH5)-ΔyeeUV, or SV164 (pGH5)-ΔhipA. The strain SV164 has the trpE allele encoding anthranilate synthase free from feedback inhibition by tryptophan. The plasmid pGH5 harbors a mutant serA gene encoding phosphoglycerate dehydrogenase free from feedback inhibition by serine. The strain SV164 (pGH5) is described in detail in U.S. Pat. No. 6,180,373.

E. coli SV164(pGH5), SV164(pGH5)-ΔyefM-yoeB, SV164(pGH5)-ΔdinJ-yafQ, SV164(pGH5)-ΔmazEF, SV164 (pGH5)-ΔrelBE, SV164(pGH5)-ΔyeeUV, or SV164(pGH5)-ΔhipA can be cultivated with shaking at 37° C. for 18 hours in a 3 ml of nutrient broth supplemented with 20 mg/ml of tetracycline (marker of pGH5 plasmid). 0.3 ml of the obtained cultures can each be inoculated into 3 ml of a fermentation medium containing tetracycline (20 mg/ml) in 20×200 mm test tubes, and cultivated at 37° C. for 48 hours with a rotary shaker at 250 rpm. After cultivation, the amount of tryptophan which accumulates in the medium can be determined by TLC as described in Example 9. The fermentation medium components are set forth in Table 3, but should be sterilized in separate groups A, B, C, D, E, F, and H, as shown, to avoid adverse interactions during sterilization.

TABLE 3

| Groups | Component | Final concentration, g/l |
|---|---|---|
| A | $KH_2PO_4$ | 1.5 |
| | NaCl | 0.5 |
| | $(NH_4)_2SO_4$ | 1.5 |
| | L-Methionine | 0.05 |
| | L-Phenylalanine | 0.1 |
| | L-Tyrosine | 0.1 |
| | Mameno (total N) | 0.07 |
| B | Glucose | 40.0 |
| | $MgSO_4 \cdot 7H_2O$ | 0.3 |
| C | $CaCl_2$ | 0.011 |
| D | $FeSO_4 \cdot 7H_2O$ | 0.075 |
| | Sodium citrate | 1.0 |
| E | $Na_2MoO_4 \cdot 2H_2O$ | 0.00015 |
| | $H_3BO_3$ | 0.0025 |
| | $CoCl_2 \cdot 6H_2O$ | 0.00007 |
| | $CuSO_4 \cdot 5H_2O$ | 0.00025 |
| | $MnCl_2 \cdot 4H_2O$ | 0.0016 |
| | $ZnSO_4 \cdot 7 H_2O$ | 0.0003 |

TABLE 3-continued

| Groups | Component | Final concentration, g/l |
|---|---|---|
| F | Thiamine HCl | 0.005 |
| G | CaCO$_3$ | 30.0 |
| H | Pyridoxine | 0.03 |

Group A had a pH of 7.1 and was adjusted with NH$_4$OH. Each group is sterilized separately, chilled, and then mixed together.

Example 11

Production of L-proline by E. coli 702ilvA-ΔyefM-yoeB, 702ilvA-ΔΔdinJ-yafQ, 702ilvA-ΔmazEF, 702ilvA-ΔrelBE, 702ilvA-ΔyeeUV, or 702ilvA-ΔhipA To test the effect of inactivation of the yefM-yoeB, dinJ-yafQ, mazEF, relBE, or hipA operon on L-proline production, DNA fragments from the chromosome of the above-described E. coli MG1655 ΔyefM-yoeB::cat, MG1655 ΔdinJ-yafQ::cat, MG1655 ΔmazEF::cat, MG1655 ΔrelBE::cat, MG1655 ΔyeeUV::cat, or MG1655 ΔhipA::cat can be transferred to the proline-producing E. coli strain 702ilvA by P1 transduction (Miller, J. H. (1972) Experiments in Molecular Genetics, Cold Spring Harbor Lab. Press, Plainview, N.Y.) to obtain the strain 702ilvA-ΔyefM-yoeB, 702ilvA-ΔdinJ-yafQ, 702ilvA-ΔmazEF, 702ilvA-ΔrelBE, 702ilvA-ΔyeeUV, or 702ilvA-ΔhipA. The strain 702ilvA has been deposited in the Russian National Collection of Industrial Microorganisms (VKPM) (Russia, 117545 Moscow, 1 Dorozhny proezd, 1) on Jul. 18, 2000 under accession number VKPM B-8012 and then converted to a deposit under the Budapest Treaty on May 18, 2001.

E. coli 702ilvA, 702ilvA-ΔyefM-yoeB, 702ilvA-ΔdinJ-yafQ, 702ilvA-ΔmazEF, 702ilvA-ΔrelBE, 702ilvA-ΔyeeUV, or 702ilvA-ΔhipA can be grown for 18-24 hours at 37° C. on L-agar plates. Then, these strains can be cultivated under the same conditions as in Example 8.

Example 12

Production of L-arginine by E. coli 382-ΔrelBE or 382-ΔyeeUV

To test the effect of inactivation of the relBE operon on L-arginine production, DNA fragments from the chromosome of the above-described E. coli MG1655 ΔrelBE::cat were transferred to the arginine-producing E. coli strain 382 by P1 transduction (Miller, J. H. (1972) Experiments in Molecular Genetics, Cold Spring Harbor Lab. Press, Plainview, N.Y.) to obtain the strain 382-ΔrelBE. The strain 382 has been deposited in the Russian National Collection of Industrial Microorganisms (VKPM) (Russia, 117545 Moscow, 1 Dorozhny proezd, 1) on Apr. 10, 2000 under accession number VKPM B-7926 and then converted to a deposit under the Budapest Treaty on May 18, 2001.

E. coli 382 and 382-ΔrelBE were each cultivated with shaking at 37° C. for 18 hours in 3 ml of nutrient broth, and 0.3 ml of the obtained cultures were inoculated into 3 ml of a fermentation medium in a 20×200 mm test tubes, and cultivated at 32° C. for 48 hours on a rotary shaker.

After the cultivation, the amount of L-arginine which had accumulated in the medium can be determined by paper chromatography using the following mobile phase: butanol:acetic acid:water=4:1:1 (v/v). A solution (2%) of ninhydrin in acetone was used as a visualizing reagent. A spot containing L-arginine was cut out, L-arginine was eluted in 0.5% water solution of CdCl$_2$, and the amount of L-arginine was estimated spectrophotometrically at 540 nm. The results of 10 independent test tube fermentations are shown in Table 4.

DNA fragments from the chromosome of the above-described E. coli MG1655 ΔyeeUV::cat were transferred to the arginine-producing E. coli strain 382 in the same way as described above and the strain 382-ΔyeeYU was obtained. E. coli 382 and 382-ΔyeeYU were cultivated for L-arginine production in the same way except that the cultivation time was 72 hours in stead of 48 hours. The results of 10 independent test tube fermentations are shown in Table 5.

It can be seen from Tables 4 and 5 that 382-ΔrelBE and 382-ΔyeeUV caused accumulation of a higher amount of L-arginine as compared with the strain 382.

The composition of the fermentation medium (g/l) was as follows:

| | |
|---|---|
| Glucose | 48.0 |
| (NH$_4$)$_2$SO$_4$ | 35.0 |
| KH$_2$PO$_4$ | 2.0 |
| MgSO$_4$•7H$_2$O | 1.0 |
| Thiamine HCl | 0.0002 |
| Yeast extract | 1.0 |
| L-isoleucine | 0.1 |
| CaCO$_3$ | 5.0 |

Glucose and magnesium sulfate were sterilized separately. CaCO$_3$ was sterilized by dry-heat at 180° C. for 2 hours. pH was adjusted to 7.0.

TABLE 4

| Strain | OD$_{540}$ | Amount of L-arginine, g/l |
|---|---|---|
| 382 | 17.5 ± 1.5 | 4.9 ± 0.5 |
| 382-ΔrelBE | 17.8 ± 1.1 | 7.2 ± 0.9 |

TABLE 5

| Strain | OD$_{540}$ | Amount of L-arginine, g/l |
|---|---|---|
| 382 | 14.7 ± 1.5 | 12.0 ± 1.0 |
| 382-ΔyeeUV | 15.7 ± 0.6 | 12.8 ± 0.8 |

DNA fragments from the chromosome of the above-described E. coli MG1655 ΔyefM-yoeB::cat, MG1655 ΔdinJ-yafQ::cat, MG1655 ΔmazEF::cat, or MG1655 ΔhipA::cat can be transferred to the arginine-producing E. coli strain 382 to inactivate the yefM-yoeB, dinJ-yafQ, or mazEF operon of the strain 382 in the same manner as described above.

Example 13

Elimination of the Cm Resistance Gene (Cat Gene) from the Chromosome of L-Amino Acid-Producing E. coli Strains with the Inactivated hipA Gene The Cm resistance gene (cat gene) can be eliminated from the chromosome of the L-amino acid-producing strain with the inactivated hipA gene by using the int-xis system. For that purpose, an L-amino acid-producing strain having DNA fragments from the chromosome of *E. coli* MG1655 ΔhipA::cat transferred by P1 transduction (see Examples 3-12), can be transformed with the plasmid pMWts-Int/Xis. Transformant clones can be selected on the LB-medium containing 100 μg/ml of ampicillin. Plates can be incubated overnight at 30° C. Transformant clones can be cured of the cat gene by spreading the separate colonies at 37° C. (at that temperature repressor CIts is partially inactivated and transcription of the int/xis genes is derepressed) followed by selection of $Cm^S Ap^R$ variants. Elimination of the cat gene from the chromosome of the strain can be verified by PCR using locus-specific primers P21 (SEQ ID NO: 57) and P22 (SEQ ID NO: 58). Conditions for PCR verification can be as described above. The PCR product obtained in the reaction with cells having the eliminated cat gene as the template, should be 0.2 kbp in length. Thus, the L-amino acid-producing strain with the inactivated hipA gene and without the cat gene can be obtained.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of an aromatic L-amino acid and a non-aromatic L-amino acid of a bacterium of the Enterobacteriaceae family can be enhanced.

The invention claimed is:

1. A method for producing an L-amino acid, comprising:
cultivating an L-amino acid producing *Escherichia coli* in a medium to produce and excrete said L-amino acid into the medium in an amount of at least 0.5 g/L, and
collecting said L-amino acid from the medium;
wherein the *Escherichia coli* has been modified to attenuate expression of a gene selected from the group consisting of yoeB, yafQ, mazF, relE, yeeV, hipA, and combinations thereof,
wherein said gene(s) encodes a toxin of a bacterial toxin-antitoxin pair,
wherein said expression is attenuated by a method selected from the group consisting of
a) introducing an insertion and/or deletion that disrupts said gene(s),
b) replacing one or more bases of the gene(s),
c) modifying an expression regulating sequence of the gene(s), and
d) combinations thereof.

2. The method according to claim 1, wherein said L-amino acid is selected from the group consisting of an aromatic L-amino acid and a non-aromatic L-amino acid.

3. The method according to claim 2, wherein said aromatic L-amino acid is selected from the group consisting of L-phenylalanine, L-tyrosine, and L-tryptophan.

4. The method according to claim 2, wherein said non-aromatic L-amino acid is selected from the group consisting of L-threonine, L-lysine, L-cysteine, L-methionine, L-leucine, L-isoleucine, L-valine, L-histidine, L-glycine, L-serine, L-alanine, L-asparagine, L-aspartate, L-glutamine, L-glutamic acid, L-proline, and L-arginine.

5. A method for producing an L-amino acid, comprising:
cultivating an L-amino acid producing *Escherichia coli* in a medium to produce and excrete said L-amino acid into the medium in an amount of at least 0.5 g/L, and
collecting said L-amino acid from the medium by a method selected from the group consisting of ion-exchange, concentration, crystallization, and combinations thereof;
wherein the *Escherichia coli* has been modified to attenuate expression of a gene selected from the group consisting of yoeB, yafQ, mazF, relE, yeeV, hipA, and combinations thereof,
wherein said gene(s) encodes a toxin of a bacterial toxin-antitoxin pair,
wherein said expression is attenuated by a method selected from the group consisting of
a) introducing an insertion and/or deletion that disrupts said gene(s),
b) replacing one or more bases of the gene(s),
c) modifying an expression regulating sequence of the gene(s), and
d) combinations thereof.

* * * * *

UNITED STATES PATENT AND TRADEMARK OFFICE
CERTIFICATE OF CORRECTION

PATENT NO. : 7,855,060 B2  
APPLICATION NO. : 11/830974  
DATED : December 21, 2010  
INVENTOR(S) : Filippov et al.

Page 1 of 1

It is certified that error appears in the above-identified patent and that said Letters Patent is hereby corrected as shown below:

On the Title Page

Section (60) on the cover page of the U.S. patent should be amended as follows:
Provisional application No. 60/723,929, filed on Oct. 6, 2005, provisional application No. 60/714,844, filed on Sep. 8, 2005, provisional application No. 60/714,849, filed on Sep. 8, 2005, provisional application No. 60/714,848, filed on Sep. 8, 2005

Column 1, line 8-25
In the first paragraph of the Specification below the title, it should read:

This application claims priority under 35 U.S.C. §119 to Russian Patent Application No. 2005104462, filed on Feb. 18, 2005, Russian Patent Application No. 2005104461, filed on Feb. 18, 2005, Russian Patent Application No. 2005104460, filed on Feb. 18, 2005, Russian Patent Application No. 2005106344, filed on Mar. 10, 2005, Russian Patent Application No. 2005109258, filed on Mar. 31, 2005, Russian Patent Application No. 2005125291, filed on Aug. 9, 2005, U.S. Provisional Patent Application No. 60/714,848, filed on Sep. 8, 2005, U.S. Provisional Patent Application No. 60/714,844, filed on Sep. 8, 2005, U.S. Provisional Patent Application No. 60/714,849, filed on Sep. 8, 2005, and U.S. Provisional Patent Application No. 60/723,929, filed on Oct. 6, 2005, and under 35 U.S.C. §120 as a continuation to PCT/JP2006/303215, filed Feb. 16, 2006, the contents of all of which are incorporated by reference in their entireties. The Sequence Listing filed electronically herewith is also hereby incorporated by reference in its entirety (File Name: US-205_Seq_List_Copy_1; File Size: 34 KB; Date Created: Jul. 31, 2007).

Signed and Sealed this  
Twenty-sixth Day of April, 2011

David J. Kappos  
*Director of the United States Patent and Trademark Office*